United States Patent
Hung et al.

(10) Patent No.: US 11,413,336 B2
(45) Date of Patent: Aug. 16, 2022

(54) COCCIDIOIDES ANTIGENS AND METHODS OF THEIR USE

(71) Applicant: Board of Regents of The University of Texas System, Austin, TX (US)

(72) Inventors: Chiung-Yu Hung, Helotes, TX (US); Gary Ostroff, Worcester, MA (US); Natalia Castro-Lopez, San Antonio, TX (US)

(73) Assignees: Board of Regents, The University of Texas System, Austin, TX (US); The University of Massachusetts, Boston, MA (US)

( * ) Notice: Subject to any disclaimer, the term of this patent is extended or adjusted under 35 U.S.C. 154(b) by 0 days.

(21) Appl. No.: 17/040,950

(22) PCT Filed: Mar. 22, 2019

(86) PCT No.: PCT/US2019/023626
§ 371 (c)(1),
(2) Date: Sep. 23, 2020

(87) PCT Pub. No.: WO2019/183500
PCT Pub. Date: Sep. 26, 2019

(65) Prior Publication Data
US 2021/0023188 A1 Jan. 28, 2021

Related U.S. Application Data

(60) Provisional application No. 62/647,370, filed on Mar. 23, 2018.

(51) Int. Cl.
A61K 39/00 (2006.01)
A61P 31/10 (2006.01)
A61K 39/39 (2006.01)

(52) U.S. Cl.
CPC .......... *A61K 39/0002* (2013.01); *A61K 39/39* (2013.01); *A61P 31/10* (2018.01); *A61K 2039/55555* (2013.01); *A61K 2039/55561* (2013.01); *A61K 2039/55583* (2013.01); *A61K 2039/70* (2013.01)

(58) Field of Classification Search
None
See application file for complete search history.

(56) References Cited

U.S. PATENT DOCUMENTS

| | | |
|---|---|---|
| 3,791,932 A | 2/1974 | Schuurs et al. |
| 3,949,064 A | 4/1976 | Bornstein et al. |
| 4,174,384 A | 11/1979 | Ullman et al. |
| 4,338,298 A | 7/1982 | Myers |
| 4,367,110 A | 1/1983 | Yoshikawa |
| 4,452,901 A | 6/1984 | Gordon et al. |

(Continued)

OTHER PUBLICATIONS

"Increase in reported coccidioidomycosis—United States, 1998-2011." *MMWR Morb Mortal Wkly Rep*, Mar. 29, 2013, 62, 217-221.

(Continued)

*Primary Examiner* — Michelle S Horning

(57) ABSTRACT

The present invention concerns methods and compositions for treating or preventing a fungal infection, particularly infection by a *Coccidioides* species. The invention provides methods and compositions for stimulating an immune response against the fungus. In certain embodiments, the methods and compositions involve a recombinant vaccine.

11 Claims, 11 Drawing Sheets

Specification includes a Sequence Listing.

(56) References Cited

U.S. PATENT DOCUMENTS

| | | |
|---|---|---|
| 4,578,770 A | 3/1986 | Mitani |
| 4,596,792 A | 6/1986 | Vyas |
| 4,599,230 A | 7/1986 | Milich et al. |
| 4,599,231 A | 7/1986 | Milich et al. |
| 4,601,903 A | 7/1986 | Frasch |
| 4,608,251 A | 8/1986 | Mia |
| 4,690,915 A | 9/1987 | Rosenberg |
| 4,748,018 A | 5/1988 | Stolle et al. |
| 5,084,269 A | 1/1992 | Kullenberg |
| 5,199,942 A | 4/1993 | Gillis |
| 5,512,282 A | 4/1996 | Krivan et al. |
| 5,548,066 A | 8/1996 | Leneau et al. |
| 5,620,896 A | 4/1997 | Herrmann et al. |
| 5,925,565 A | 7/1999 | Berlioz et al. |
| 5,935,819 A | 8/1999 | Eichner et al. |
| 5,958,895 A | 9/1999 | Pachuk et al. |
| 6,651,655 B1 | 11/2003 | Licalsi et al. |
| 6,656,462 B2 | 12/2003 | Dondero et al. |
| 6,733,754 B2 | 5/2004 | Roberts et al. |
| 6,756,361 B1 | 6/2004 | Fattom et al. |
| 6,770,278 B1 | 8/2004 | Skelly |
| 6,793,923 B2 | 9/2004 | Brown et al. |
| 6,814,971 B2 | 11/2004 | Roberts et al. |
| 6,936,258 B1 | 8/2005 | Pavliak et al. |
| 7,332,324 B2 | 2/2008 | Cole et al. |
| 2004/0001843 A1 | 1/2004 | Galgiani et al. |

OTHER PUBLICATIONS

Abuodeh et al., "Resistance to Coccidioides immitis in Mice after Immunization with Recombinant Protein or a DNA Vaccine of a Proline-Rich Antigen" *Infection and Immunity* 1999, 67, 2935-40.

Azmi et al., "Recent progress in adjuvant discovery for peptide-based subunit vaccines" *Human Vaccines & Immunotherapeutics* 2014, 10, 778-96.

Cole et al., "A vaccine against coccidioidomycosis is justified and attainable" *Medical Mycology* 2004, 42, 189-216.

Cole et al., "Progress Toward a Human Vaccine Against Coccidioidomycosis" *Curr Fungal Infect Rep.* 2012, 6(4), 235-244.

Da Silva et al., "TLR-2 and IL-17A in chitin-induced macrophage activation and acute inflammation." *J Immunol* 2008, 181, 4279-4286.

Galgiani et al., "2016 Infectious Diseases Society of America (IDSA) Clinical Practice Guideline for the Treatment of Coccidioidomycosis" *Clinical Infectious Diseases* 2016, 63, e112-46.

Gow et al., "The Fungal Cell Wall: Structure, Biosynthesis, and Function" *Microbiol Spectr* 2017, 5, 25 pages.

Herr et al., "Evaluation of two homologous proline-rich proteins of Coccidioides posadasii as candidate vaccines against coccidioidomycosis." *Infection and

FIGS. 1A-C

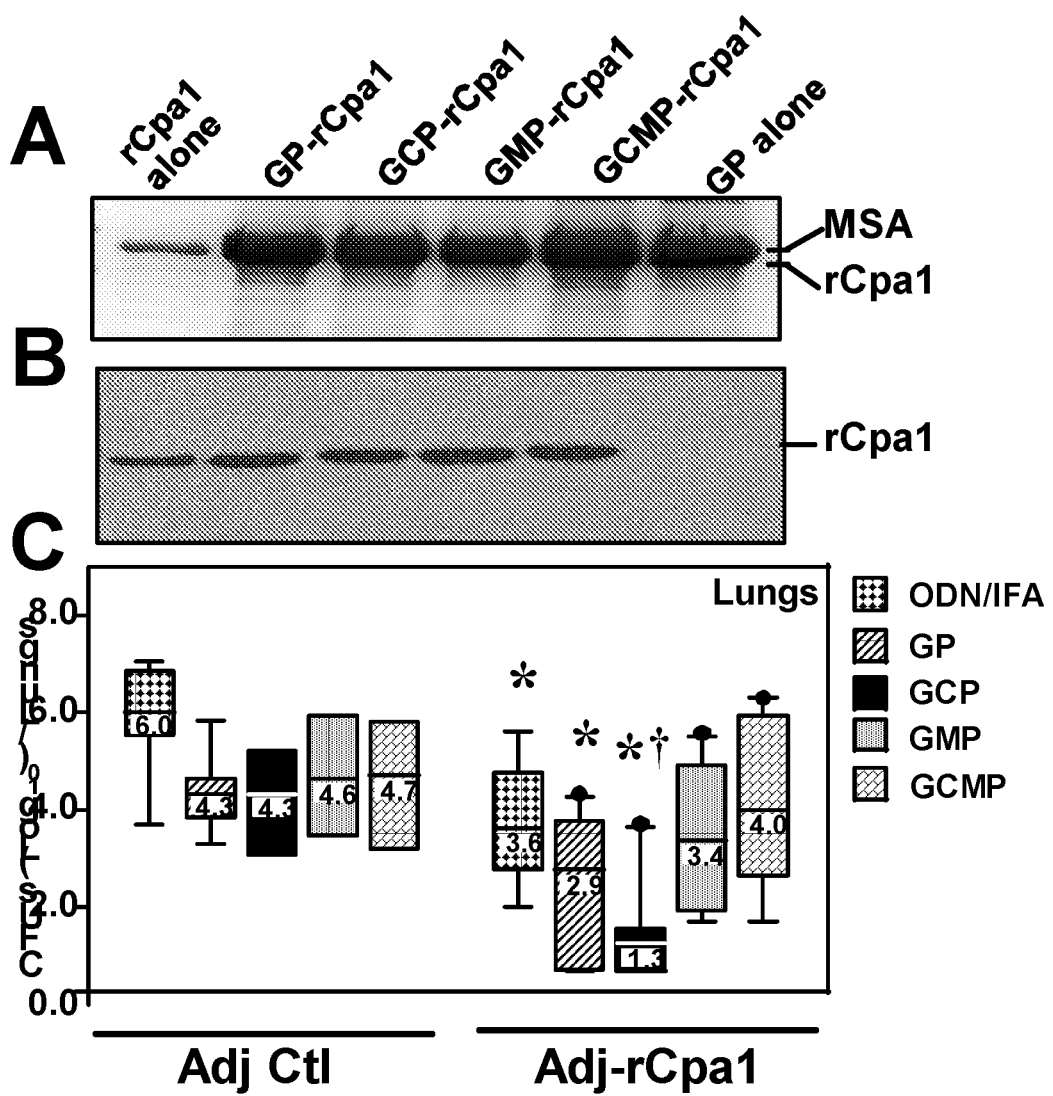
FIGS. 2A-C

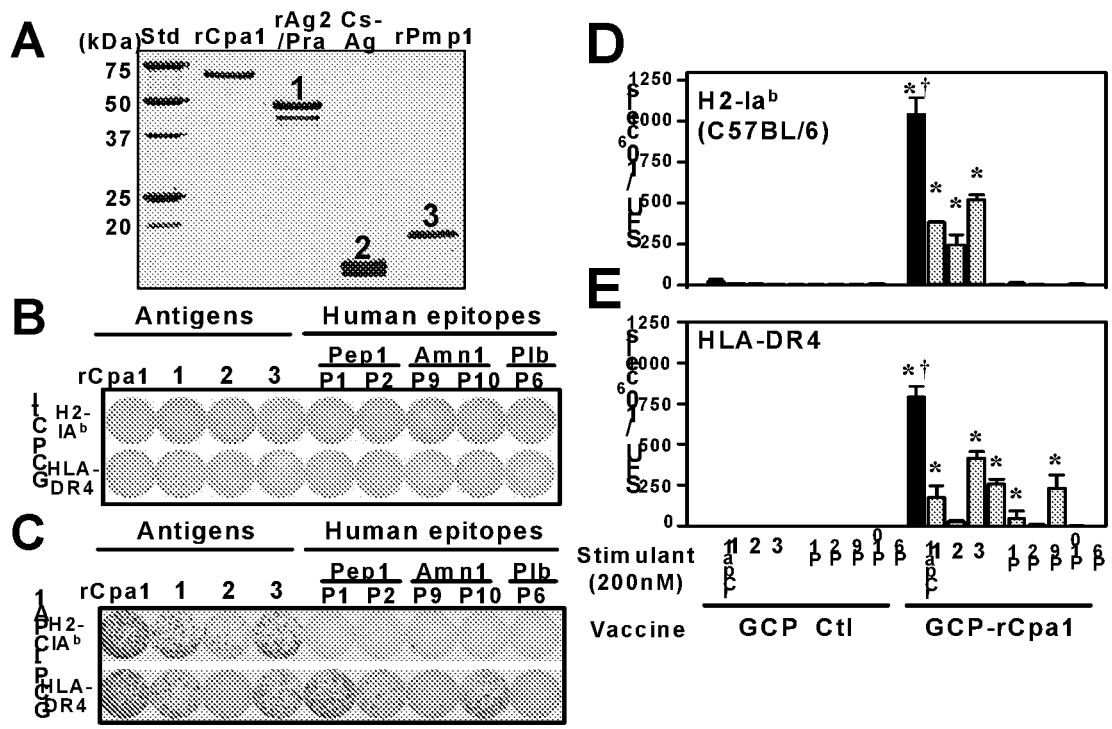
FIGS. 3A-E
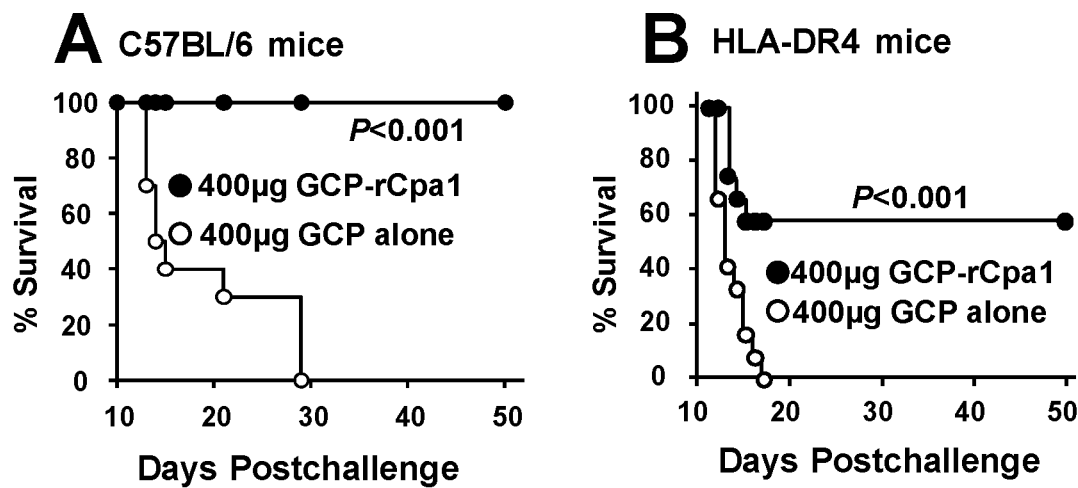
FIGS. 4A-B

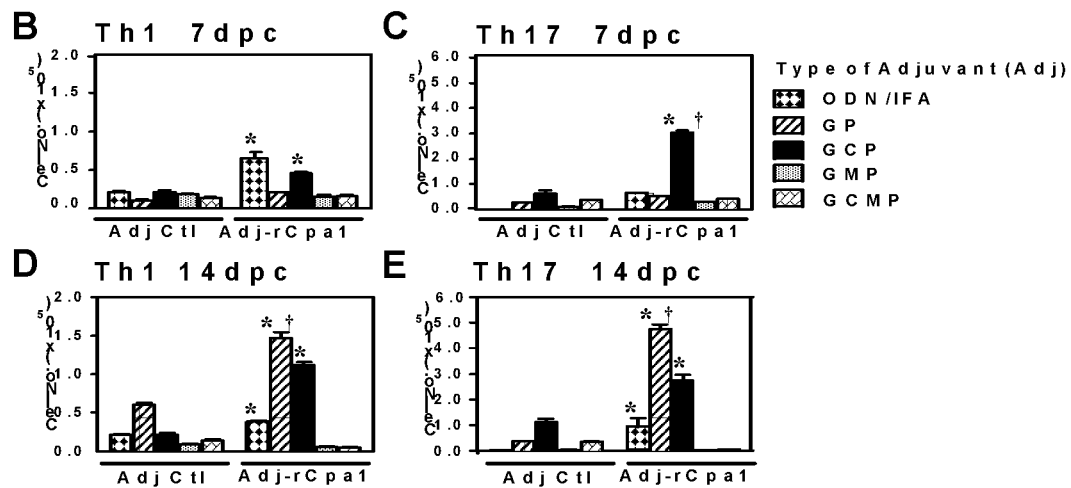
FIG. 6B-E
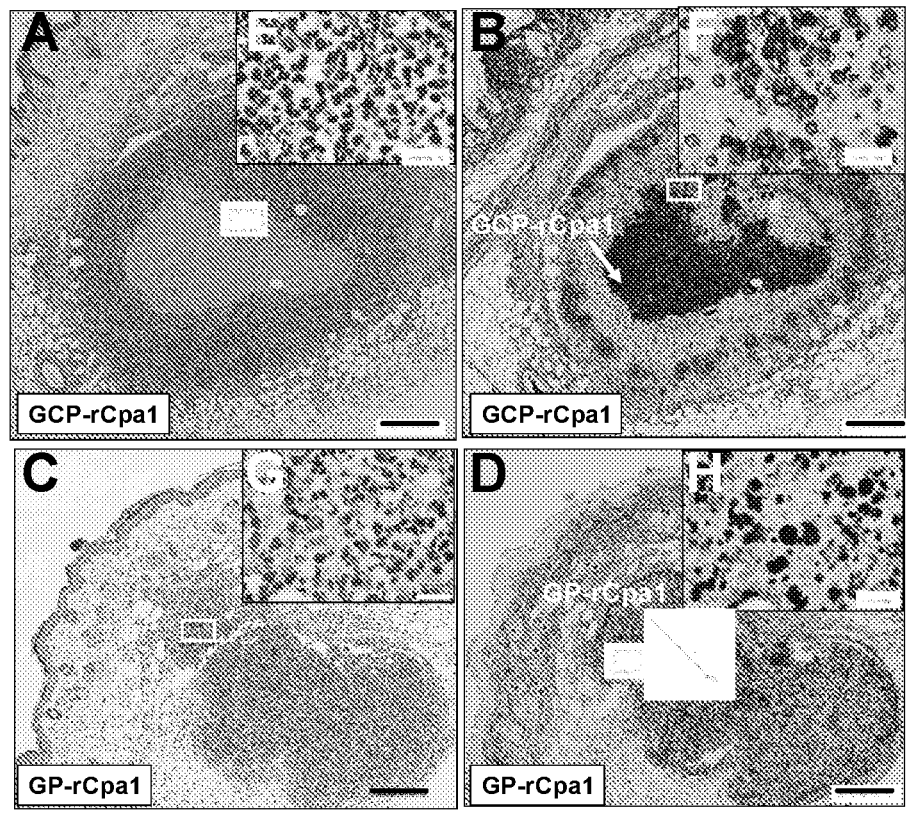
FIGS. 7A-H

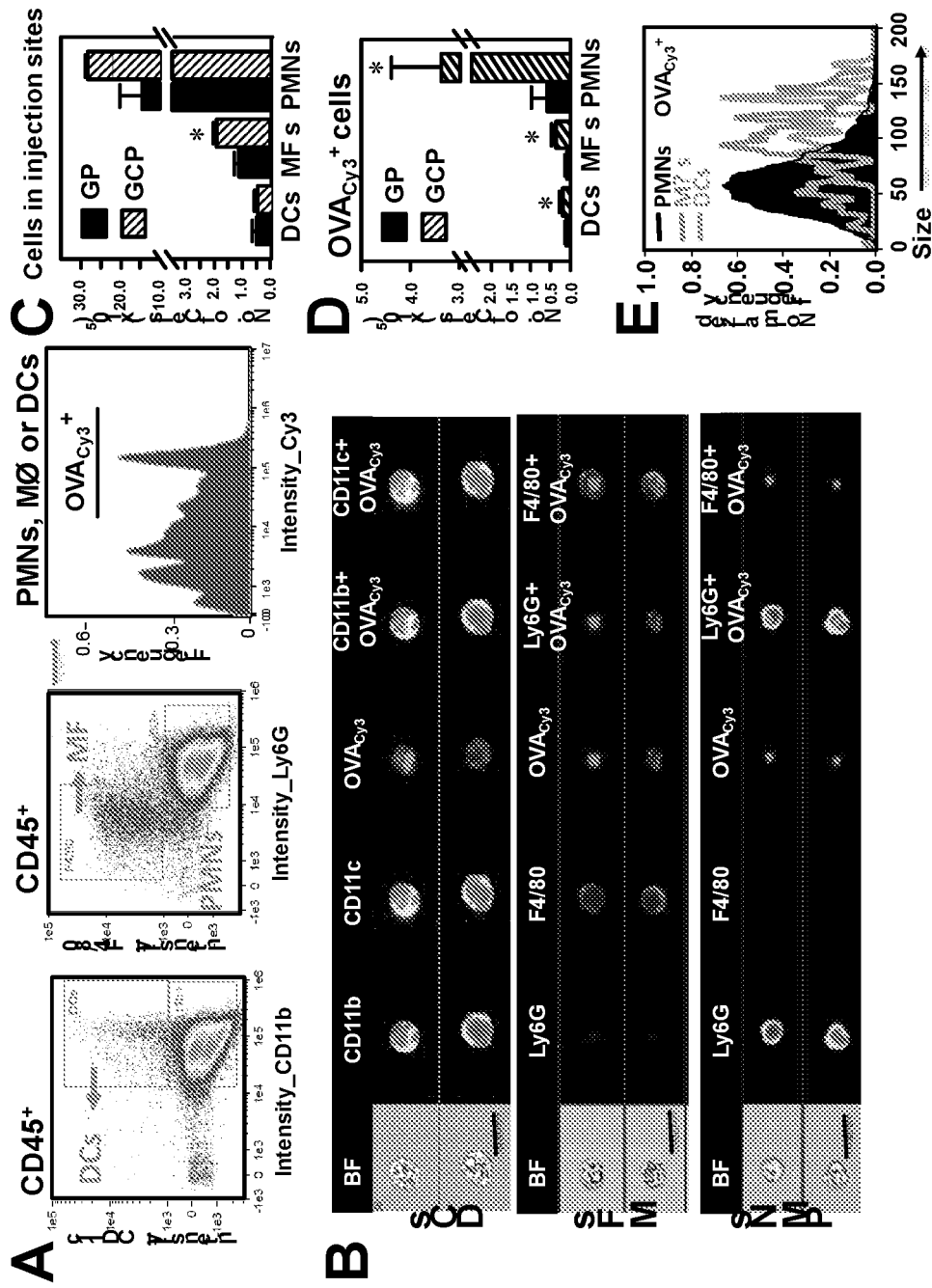
FIGS. 8A-E

| | | |
|---|---|---|
| 1 | MGSSHHHHHHSSGLVPRGSHMGPGPGMQFSHALIALVAAGLASAQLPDIP | 50 |
| 51 | PCALNCFVEALGNDGCTRLTDFKCHCSKPELPGQITPCVEEACPLDARIS | 100 |
| 101 | VSNIVVDQCSKAGVPIDIPPVDTTAAPEPSETGPGPGMKFSLLSAIAAAV | 150 |
| 151 | FVPFTSATPLASTADLSYDTHYDDPSLPLSGVTCSDGDNGMITKGYNTAG | 200 |
| 201 | EIPNYPHVGGAFTVETWNSPNCGKCYKVTYNAKTIFLTAIDHSNSGFNIA | 250 |
| 251 | KKSMDVLTNGRAEELGRIKVTYEEVASSLCGLKGPGPGMASLKAGDSFPS | 300 |
| 301 | DVVFSYIPWTPDNKDIKACGMPQNYEASKLWADKKVVLFSLPGAFTPTCS | 350 |
| 351 | ASHLPGYIQKLPQLKEKGVDVVAVLAFNDAWVMSAWGKANGVTGDDILFL | 400 |
| 401 | SDPEAKFSKSIGWNAGERTGRYAMIIDHGQVTYAEIEPGREVTVSGADAV | 450 |
| 451 | ISKLGPGPGMRNSILLAATVLLGCTSAKVHGPGPGHVRALGQKYFGSLPS | 500 |
| 501 | SQQQTVGPGPGPAKVDVLLAQSLKLADVLKFGPGPGNGLATTGTLVLEWT | 550 |
| 551 | RLSDITGPGPGTPLVVYIPNYPYTTWSNISTGPGPG | 586 |

FIG. 9A

| Antigen | Corresponding position in rCPA1 sequence and length(aa) | Genbank accession numbers/ amino acid sequences of antigens |
|---|---|---|
| 1. rCPA1 | 1-586 | KY883768 |
| 1. Ag2/Pra | 27-132 (106 aa) | XP_003069153 |
| 2. Cs-Ag | 138-283 (146 aa) | XP_003065978 |
| 3. Pmp | 289-454 (166 aa) | XP_003069274 |
| 4. Pep1-P1 | 460-480 (21 aa) | MRNSILLAATVLLGCTSAKVH (SEQ ID NO:3) |
| 5. Pep1-P2 | 486-506 (21 aa) | HVRALGQKYFGSLPSSQQQTV (SEQ ID NO:4) |
| 6. Amn1-P10 | 512-531 (20 aa) | PAKVDVLLAQSLKLADVLKF (SEQ ID NO:5) |
| 7. Amn1-P11 | 537-556 (20 aa) | NGLATTGTLVLEWTRLSDIT (SEQ ID NO:6) |
| 8. Plb-P6 | 562-581 (20 aa) | TPLVVYIPNYPYTTWSNIST (SEQ ID NO:7) |

FIG. 9B

COCCIDIOIDES ANTIGENS AND METHODS OF THEIR USE

PRIORITY DATA

This Application is a national phase application under 35 U.S.C. § 371 of International Patent Application No. PCT/US2019/023626, filed Mar. 22, 2019 which claims priority to U.S. Provisional Application Ser. No. 62/647,370 filed Mar. 23, 2018, which is incorporated by reference in its entirety.

STATEMENT OF GOVERNMENT SUPPORT

This invention was made with government support under 1R21AI114762-01A1 awarded by the National Institutes of Health. The government has certain rights in the invention.

BACKGROUND OF THE INVENTION

I. Field of the Invention

The present invention relates generally to the fields of immunology, microbiology, and pathology. More particularly, it concerns methods and compositions involving recombinant antigens, which can be used to invoke an immune response against a *Coccidioides* fungus.

II. Background

There is an urgent unmet need to develop an effective vaccine against *Coccidioides* infection, which continues to be a major cause of morbidity within endemic areas. Currently, there is no *Coccidioides* vaccine approved for general use.

Coccidioidomycosis, commonly known as San Joaquin Valley fever affects residents in semi-arid to arid regions of the southwestern United States, northern Mexico, and scattered areas of Central and South America. The incidence of reported coccidioidomycosis has increased substantially from 5.3 to 42.6 per 100,000 population in the southwestern US from 1998 to 2011. An estimated 150,000 people in the United States become infected with *Coccidioides* annually. In the endemic areas 17-29% of community-acquired pneumonia cases are due to *Coccidioides* infection. Recent epidemiological studies show that the geographic range of coccidioidomycosis is expanding, as new cases have been identified in the state of Washington, well outside the historically endemic areas. Collectively, these statistics highlight the increasing health- and cost-related impacts of coccidioidomycosis as a major public health challenge. Thus, there is an urgent unmet need to develop a human vaccine against *Coccidioides* infection.

A number of experimental vaccines have been previously generated and evaluated in genetically susceptible murine models of coccidioidomycosis, including formalin-killed spherules (FKS), live spores isolated from attenuated strains of this pathogen, chemical extracts of spherules and recombinant antigens mixed with an adjuvant. The use of recombinant antigens in vaccines is attractive due to their well-defined chemical composition and low risk for adverse effects. Several recombinant antigens of *Coccidioides posadasii* including cell wall antigen 2 (Ag2/Pra), proline-rich protein 2 (Prp2), *Coccidioides*-specific antigen (Cs—Ag), proximal matrix protein 1 (Pmp1), urease (Ure), β-1,3-glucanosyltransferase (Gel1), aspartyl protease 1 (Pep1), α-mannosidase 1 (Amn1), and phospholipase B (Plb) have been evaluated using a murine model of coccidioidomycosis. Although each individual antigen has shown moderate but significant protective efficacy, a multivalent polypeptide antigen that can induce large repertories of specific B-cell and T-cell responses might be more effective.

Recombinant protein antigens elicit a relatively weak immune response, and thus require the use of an adjuvant to optimize protective efficacy. The inventors have created a genetically engineered live, attenuated vaccine (ΔT) to explore the nature of vaccine immunity in mice after intranasal challenge with a potentially lethal dose of *Coccidioides* spores. While mice lacking IFN-γ or IL-4 receptors could develop comparable vaccine immunity without loss of ΔT vaccine-induced resistance, deficiency of IL-17A and IL-17 receptor resulted in increased susceptibility to *Coccidioides* infection. These data suggest that vaccine-induced CD4$^+$ T cells, particularly Th17 cells are essential for vaccine immunity against *Coccidioides* infection.

Several types of purified, porous yeast cell-wall particles have been generated for vaccine development. Pure β-glucan particles (GPs) and glucan-mannan particles (GMPs) are derived from *Saccharomyces cerevisiae*, whereas glucan-chitin particles (GCPs) and glucan-chitin-mannan particles (GCMPs) are produced from *Rhodotorula mucilaginosa*, a non-pathogenic yeast. Notably, these particles have shown to be safe in both preclinical and human trials. GPs are phagocytosed via complement and Dectin-1 activation through interactions with β-glucan. Intranasal administration of GCPs and GMPs stimulates mice to produce significantly higher amounts of IL-6 and MCP-1 (CCL2) in bronchoalveolar lavage compared to GPs, suggesting that GCPs and GMPs may augment Th17 immunity.

SUMMARY OF THE INVENTION

In addressing the problems associated with *Coccidioides* infection the inventors developed an effective vaccine against *Coccidioides* infection. Disclosed herein is a designed and expressed multivalent, recombinant *Coccidioides* polypeptide antigen (rCpa1) that consists of the most immunogenic fragment of Ag2/Pra, the full lengths of Cs—Ag and Pmp1, and 5 promiscuous, immunodominant T cell epitopes derived from Pep1, Amn1, and Plb of *Coccidioides posadasii* (6, 9-11, 21). Also disclosed herein is a an adjuvant/delivery system made of yeast cell-wall particles containing β-glucan and chitin that can augment Th17 immunity to improve protective efficacy of the newly created multivalent antigen (rCpa1) against *Coccidioides* infection. Specifically, the protective efficacy and immunoreactivity of experimental vaccines including or consisting of rCpa1 encapsulated in four types of yeast cell-wall particles (GPs, GCPs, GMPs, GCMPs) and an oligonucleotide adjuvant containing 2 copies of a CpG motif (ODN) that has been shown to stimulate a predominant Th1 response against *Coccidioides* infection (11, 22). The adjuvant/delivery system can encapsulate purified rCpa1 into four types of yeast cell-wall particles containing various compositions of β-glucan, mannan, and chitin and/or mixed with an oligonucleotide (ODN) containing 2 methylated dinucleotide CpG motifs. The multivalent antigen encapsulating rCpa1 into glucan-chitin particles (GCP-rCpa1) showed a significantly elevated reduction of fungal burden for human HLA-DR4 transgenic mice compared to the other tested adjuvant-rCpa1 formulations. The rCpa1 vaccine can provide a comparable degree of survival to a live, attenuated vaccine for both genetically susceptible C57BL/6 and HLA-DR4 transgenic mice against pulmonary coccidioidomycosis.

Among the tested adjuvants, GCPs and GPs were both capable of stimulating Th17 response. Mice vaccinated with GCP-rCpa1 showed elevated IL-17 production in T-cell recall assays and early lung infiltration of activated Th1 and Th17 cells compared to GP-rCpa1-vaccinated mice. Concurringly, GCP-rCpa1 vaccine stimulated enhanced infiltration of macrophages to engulf and process the vaccine for antigen presentation in the injection sites compared to GP-rCpa1 injection.

Certain embodiments are directed to an immunogenic composition comprising an antigen as described herein.

In some aspects, the recombinant antigen disclosed herein is at least 80% identical to an amino acid sequence of SEQUENCE TABLE NO. 1 (SEQ ID NO:2). In further aspects, the recombinant antigen disclosed herein is at least 85, 90, 95, 98, 99, of 100% identical to an amino acid sequence of SEQUENCE TABLE NO. 1 (SEQ ID NO:2).

In further embodiments, the immunogenic composition further comprises one or more additional *Coccidioides* antigen(s). In additional embodiments, the immunogenic composition may also include an adjuvant. In particular embodiments, the additional *Coccidioides* antigen(s) is one or more of Ag2/Pra, Pra2, Cs—Ag, Ure, Gel1, Pmp1, Pep1, Amn1, and/or Plb.

In further embodiments, a polynucleotide molecule comprising a nucleic acid sequence encoding a recombinant antigen disclosed herein is contemplated. In further aspects, an expression vector comprises the nucleic acid sequence operably linked to an expression control sequence. In still further aspects, a host cell comprising the expression vector is also contemplated.

Embodiments include the use of the composition, the recombinant polypeptide, the polynucleotide molecule and/or the expression vector described herein to treat or prevent a *Coccidioides* infection in a subject.

In some embodiments, a method to manufacture an immunogenic composition comprising the recombinant antigen disclosed herein is contemplated.

Embodiments include the use of the recombinant antigen described herein in methods and compositions for the treatment of fungal and/or *Coccidioides* infection. Furthermore, certain embodiments provide methods and compositions that can be used to treat (e.g., limiting *Coccidioides* growth and/or persistence in a subject) or prevent fungal infection. In some cases, methods for stimulating an immune response involve administering to the subject an effective amount of the immunogenic composition described herein and in certain aspects other fungal proteins.

In other aspects, the subject can be administered with the immunogenic composition, the recombinant antigen, or the vector described herein. The recombinant antigen or the vector can be formulated in a pharmaceutically acceptable composition. The composition can further comprise one or more additional *Coccidioides* antigens or immunogenic fragments thereof.

In still further aspects, the recombinant antigen described herein is multimerized, e.g., dimerized or a linear fusion of two or more polypeptides or peptide segments. In certain aspects of the invention, a composition comprises multimers or concatamers of 1, 2, 3, 4, 5, 6, 7, 8, 9, 10, 11, 12, 13, 14, 15, 16, 17, 18, 19, 20 or more proteins or segments thereof. Concatamers are linear polypeptides having one or more repeating peptide units. The at proteins or peptide fragments can be consecutive or separated by a spacer or other peptide sequences, e.g., one or more additional fungal peptides. In a further aspect, the other polypeptides or peptides contained in the multimer or concatamer can include, but are not limited to Ag2/Pra, Pra2, Cs—Ag, Ure, Gel1, Pmp1, Pep1, Amn1, and/or Plb, or immunogenic fragments thereof.

Certain embodiments include methods for eliciting an immune response against a *Coccidioides* fungus in a subject comprising providing to the subject an effective amount of an immunogenic composition or a recombinant antigen disclosed herein.

Embodiments of the invention include compositions that include a polypeptide, peptide, or protein that comprises a sequence that is or is at least 70%, 75%, 80%, 85%, 90%, 95%, 96%, 97%, 98%, or 99% identical or similar to a recombinant antigen disclosed herein, in particular see, SEQUENCE TABLE NO. 1 (SEQ ID NOs:2). Similarity or identity, with identity being preferred, is known in the art and a number of different programs can be used to identify whether a protein (or nucleic acid) has sequence identity or similarity to a known sequence. Sequence identity and/or similarity is determined using standard techniques known in the art, including, but not limited to, the local sequence identity algorithm of Smith and Waterman (1981), by the sequence identity alignment algorithm of Needleman and Wunsch (1970), by the search for similarity method of Pearson and Lipman (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al. (1984), preferably using the default settings, or by inspection. Preferably, percent identity is calculated by using alignment tools known to and readily ascertainable to those of skill in the art. Percent identity is essentially the number of identical amino acids divided by the total number of amino acids compared times one hundred.

Still further embodiments include methods for stimulating in a subject a protective or therapeutic immune response against a *Coccidioides* fungus comprising administering to the subject an effective amount of a composition including a recombinant antigen disclosed herein or a homologue thereof; or, (ii) a nucleic acid molecule comprises a sequence encoding a recombinant antigen disclosed herein or homologue thereof, or (iii) administering any of (i)-(ii) with any combination or permutation of fungal proteins described herein. In certain aspects the subject is a human or a cow. In a further aspect the composition is formulated in a pharmaceutically acceptable formulation.

Yet still further embodiments include vaccines comprising a pharmaceutically acceptable composition having a recombinant antigen described herein, or any other combination or permutation of protein(s) or peptide(s) described herein, wherein the composition is capable of stimulating an immune response against a *Coccidioides* fungus. The vaccine may comprise recombinant antigen described herein, or any other combination or permutation of protein(s) or peptide(s) described. In certain aspects, a recombinant antigen described herein, or any other combination or permutation of protein(s) or peptide(s) described, are multimerized, e.g., dimerized or concatamerized. In a further aspect, the vaccine composition is contaminated by less than about 10, 9, 8, 7, 6, 5, 4, 3, 2, 1, 0.5, 0.25, 0.05% (or any range derivable therein) of other *Coccidioides* proteins. Typically the vaccine comprises an adjuvant. In certain aspects a protein or peptide of the invention is linked (covalently or non-covalently) to the adjuvant, preferably the adjuvant is chemically conjugated to the protein.

In still yet further embodiments, a vaccine composition is a pharmaceutically acceptable composition having a recombinant nucleic acid encoding a recombinant antigen described herein, or any other combination or permutation of protein(s) or peptide(s) described herein, wherein the composition is capable of stimulating an immune response against a *Coccidioides* fungus. In certain embodiments the recombinant nucleic acid contains a heterologous promoter. Preferably the recombinant nucleic acid is a vector. More preferably the vector is a plasmid or a viral vector. The vaccine may comprise a pharmaceutically acceptable excipient, more preferably an adjuvant.

Still further embodiments include methods for stimulating in a subject a protective or therapeutic immune response against a *Coccidioides* fungus comprising administering to the subject an effective amount of a recombinant antigen described herein, or a nucleic acid encoding the same, and further comprising one or more of a Ag2/Pra, Pra2, Cs—Ag, Ure, Gel1, Pmp1, Pep1, Amn1, and/or Plb protein or peptide thereof. In a further aspect the composition is formulated in a pharmaceutically acceptable formulation. The *Coccidioides* for which a subject is being treated may be *Coccidioides posadasii*.

In certain aspects an antigen combination can include (1) a recombinant antigen disclosed herein and Ag2/Pra; (2) a recombinant antigen disclosed herein and Pra2; (3) a recombinant antigen disclosed herein and Cs—Ag; (4) a recombinant antigen disclosed herein and Ure; (5) a recombinant antigen disclosed herein and Gel1; (6) a recombinant antigen disclosed herein and Pmp1; (7) a recombinant antigen disclosed herein and Pep1; (8) a recombinant antigen disclosed herein and Amn 1; and/or (9) a recombinant antigen disclosed herein and Plb.

An immune response refers to a humoral response, a cellular response, or both a humoral and cellular response in an organism. An immune response can be measured by assays that include, but are not limited to, assays measuring the presence or amount of antibodies that specifically recognize a protein or cell surface protein, assays measuring T-cell activation or proliferation, and/or assays that measure modulation in terms of activity or expression of one or more cytokines.

In yet still further embodiments of the invention a composition may include a polypeptide, peptide, or protein that is or is at least 70%, 75%, 80%, 85%, 90%, 95%, 96%, 97%, 98%, or 99% identical or similar to a recombinant antigen disclosed herein.

In certain aspects, a polypeptide or segment/fragment can have a sequence that is at least 85%, at least 90%, at least 95%, at least 98%, or at least 99% or more identical to the amino acid sequence of the reference recombinant polypeptide. The term "similarity" refers to a polypeptide that has a sequence that has a certain percentage of amino acids that are either identical with the reference polypeptide or constitute conservative substitutions with the reference polypeptides.

The polypeptides described herein may include 1, 2, 3, 4, 5, 6, 7, 8, 9, 10, 11, 12, 13, 14, 15, or more variant amino acids within at least, or at most 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 300, 400, 500, 550, 1000 or more contiguous amino acids, or any range derivable therein, of the sequence of SEQUENCE TABLE NO. 1 (SEQ ID NO: 1).

A polypeptide segment as described herein may include 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 300, 400, 500, 550, 1000 or more contiguous amino acids, or any range derivable therein, of the sequence of SEQUENCE TABLE NO. 1 (SEQ ID NO: 1).

In yet still further embodiments, a composition may include a polynucleotide that is or is at least 70%, 75%, 80%, 85%, 90%, 95%, 96%, 97%, 98%, or 99% identical or similar to a nucleic acid sequence encoding a recombinant antigen disclosed herein. In certain aspects, the nucleic acid sequence will have all or part of the nucleic acid sequence provided herein.

The compositions may be formulated in a pharmaceutically acceptable composition.

In further aspects, a composition may be administered more than one time to the subject, and may be administered 1, 2, 3, 4, 5, 6, 7, 8, 9, 10, 15, 20 or more times. The administration of the compositions include, but is not limited to oral, parenteral, subcutaneous, intramuscular, intravenous, or various combinations thereof, including inhalation or aspiration.

In still further embodiments, a composition comprises a recombinant nucleic acid molecule encoding a polypeptide described herein or segments/fragments thereof. Typically a recombinant nucleic acid molecule encoding a polypeptide described herein contains a heterologous promoter. In certain aspects, a recombinant nucleic acid molecule of the invention is a vector, in still other aspects the vector is a plasmid. In certain embodiments the vector is a viral vector. A composition is typically administered to mammals, such as human subjects, but administration to other animals that are capable of eliciting an immune response is contemplated. In further embodiments the immune response is a protective immune response.

In further embodiments a composition comprises a recombinant nucleic acid molecule encoding all or part of a recombinant antigen disclosed herein or variant thereof. Additional *Coccidioides* antigens that can be used in combination with the polypeptides described herein include, but are not limited to Ag2/Pra, Pra2, Cs—Ag, Ure, Gel1, Pmp1, Pep1, Amn1, and/or Plb.

Compositions discussed herein are typically administered to human subjects, but administration to other animals that are capable of eliciting an immune response to a *Coccidioides* fungi is contemplated, particularly cattle, horses, goats, sheep and other domestic animals, i.e., mammals.

In certain embodiments the immune response is a protective immune response. In still further aspects, the methods and compositions of the invention can be used to prevent, ameliorate, reduce, or treat infection of tissues or glands, e.g., lungs, and other infections. Other methods include, but are not limited to prophylactically reducing fungal burden in a subject not exhibiting signs of infection, particularly those subjects suspected of or at risk of being colonized by a target fungus, e.g., patients that are or will be at risk or susceptible to infection during a hospital stay, treatment, and/or recovery.

Any embodiment discussed with respect to one aspect of the invention applies to other aspects of the invention as well. In particular, any embodiment discussed in the context of a composition comprising a recombinant antigen disclosed herein or a nucleic acid encoding the same may be implemented with respect to other antigens, such as Ag2/Pra, Pra2, Cs—Ag, Ure, Gel1, Pmp1, Pep1, Amn1, and/or Plb. These other antigens can also be specifically excluded from a claimed composition.

Embodiments include compositions that contain or do not contain a fungi. A composition may or may not include an attenuated or viable or intact *Coccidioides* fungi. In certain aspects, the composition comprises a fungi that is not a *Coccidioides* fungi or does not contain *Coccidioides* fungi. In certain embodiments a fungal composition comprises a recombinantly expressed antigen described herein or a nucleotide encoding the same. The composition may be or include a recombinantly engineered *Coccidioides* fungus that has been altered in a way that comprises specifically altering the fungus with respect to a virulence factor or cell surface protein. For example, the fungus may be recombinantly modified to express more of the virulence factor or cell surface protein than it would express if unmodified.

The term "isolated" can refer to a nucleic acid or polypeptide that is substantially free of cellular material, bacterial material, viral material, or culture medium (when produced by recombinant DNA techniques) of their source of origin, or chemical precursors or other chemicals (when chemically synthesized). Moreover, an isolated compound refers to one that can be administered to a subject as an isolated compound; in other words, the compound may not simply be considered "isolated" if it is adhered to a column or embedded in an agarose gel. Moreover, an "isolated nucleic acid fragment" or "isolated peptide" is a nucleic acid or protein fragment that is not naturally occurring as a fragment and/or is not typically in the functional state.

Moieties, such as polypeptides, peptides, antigens, or immunogens, may be conjugated or linked covalently or noncovalently to other moieties such as adjuvants, proteins, peptides, supports, fluorescence moieties, or labels. The term "conjugate" or "immunoconjugate" is broadly used to define the operative association of one moiety with another agent and is not intended to refer solely to any type of operative association, and is particularly not limited to chemical "conjugation." Recombinant fusion proteins are particularly contemplated. Compositions of the invention may further comprise an adjuvant or a pharmaceutically acceptable excipient. An adjuvant may be covalently or non-covalently coupled to a polypeptide or peptide of the invention. In certain aspects, the adjuvant is chemically conjugated to a protein, polypeptide, or peptide.

As used herein, the term "modulate" or "modulation" encompasses the meanings of the words "enhance," or "inhibit." "Modulation" of activity may be either an increase or a decrease in activity. As used herein, the term "modulator" refers to compounds that effect the function of a moiety, including up-regulation, induction, stimulation, potentiation, inhibition, down-regulation, or suppression of a protein, nucleic acid, gene, organism or the like.

The term "providing" is used according to its ordinary meaning to indicate "to supply or furnish for use." In some embodiments, the protein is provided directly by administering the protein, while in other embodiments, the protein is effectively provided by administering a nucleic acid that encodes the protein. In certain aspects the invention contemplates compositions comprising various combinations of nucleic acid, antigens, peptides, and/or epitopes.

The subject can have (e.g., are diagnosed with a *Coccidioides* infection), can be suspected of having, or can be at risk of developing a *Coccidioides* infection. Compositions of the present invention include immunogenic compositions wherein the antigen(s) or epitope(s) are contained in an amount effective to achieve the intended purpose. More specifically, an effective amount means an amount of active ingredients necessary to stimulate or elicit an immune response, or provide resistance to, amelioration of, or mitigation of infection. In more specific aspects, an effective amount prevents, alleviates or ameliorates symptoms of disease or infection, or prolongs the survival of the subject being treated. Determination of the effective amount is well within the capability of those skilled in the art, especially in light of the detailed disclosure provided herein. For any preparation used in the methods of the invention, an effective amount or dose can be estimated initially from in vitro studies, cell culture, and/or animal model assays. For example, a dose can be formulated in animal models to achieve a desired immune response or circulating antibody concentration or titer. Such information can be used to more accurately determine useful doses in humans.

The embodiments in the Example section are understood to be embodiments of the invention that are applicable to all aspects of the invention.

The use of the term "or" in the claims is used to mean "and/or" unless explicitly indicated to refer to alternatives only or the alternatives are mutually exclusive, although the disclosure supports a definition that refers to only alternatives and "and/or." It is also contemplated that anything listed using the term "or" may also be specifically excluded.

Throughout this application, the term "about" is used to indicate that a value includes the standard deviation of error for the device or method being employed to determine the value.

Following long-standing patent law, the words "a" and "an," when used in conjunction with the word "comprising" in the claims or specification, denotes one or more, unless specifically noted.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

So that the matter in which the above-recited features, advantages and objects of the invention as well as others which will become clear are attained and can be understood in detail, more particular descriptions and certain embodiments of the invention briefly summarized above are illustrated in the appended drawings. These drawings form a part of the specification. It is to be noted, however, that the appended drawings illustrate certain embodiments of the invention and therefore are not to be considered limiting in their scope.

FIGS. 1A-C—Construct, expression and antibody reactivity of the newly designed rCpa1 protein. Schematic design of the rCpa1 vaccine antigen (A) and its expression, purification (B) and antibody reactivity (C). The three selected *Coccidioides* antigens (i.e., Ag2/Pra, Cs—Ag, and Pmp1) and five previously identified epitope peptides were linked with a glycine/proline spacer sequence (GPGPG) located at the C termini of each peptides (A). The first 20-residue fragment at the N-terminus of rCpa1 protein was derived from the translated pET28b plasmid vector and includes a histidine motif for nickel-affinity purification of the *E. coli*-expressed recombinant protein. SDS-PAGE separation of the rCpa1 protein. Standard (Std) and total lysates (T) of *E. coli* transformed with the pET28b-CPA1 plasmid vector construct, solubilized extract of bacterial inclusion bodies (I.B.) and the nickel affinity-purified rCpa1 are shown (B). Results of ELISA of human control sera (n=6) and sera from patients with confirmed *Coccidioides* infection (n=8), each reacted with the purified rCpa1 protein (C). The data are presented as boxplots with the 25th and 75th percentiles, respectively. A horizontal line within the boxes indicates the mean absorbance at 450 nm. The asterisk indicates a statistically significant difference between the mean absorbance values of control and patient sera.

FIGS. 2A-C—Vaccination with GCP-rCpa1 offered the highest reduction of fungal burden for HLA-DR4 transgenic mice. The purified rCpa1 was equally loaded into four types of yeast cell-wall particles. The protein contents of GPs, GCPs, GMPs and GCMPs loaded with rCpa1 protein (63 kDa) and murine serum albumin (MSA; 67 kDa) plus tRNA were revealed by Coomassie brilliant stained SDS-PAGE (A) and immunoblot with an anti-His-Tag antibody (B). Lane 1 contained 1 μg of the purified rCpa1 protein. Lanes 2-5 were loaded with protein extracts from 10% of a dose of each vaccine preparations. A protein extract from GPs loaded with only MSA plus yeast tRNA was also analyzed (GP alone). A duplicated gel was used for immunoblot using an anti-His-tag mAb, the optical densities of Lanes 1-5 were comparable, indicating equal amounts of rCpa1 protein were efficiently loaded in each type of yeast cell-wall particles (B). *Coccidioides* CFUs were detected by dilution plate culture of lung homogenates obtained from mice that were vaccinated with rCpa1 formulated in one of the five selected adjuvants (i.e., ODN/IFA, GPs, GCPs, GMPs, and GCMPs) (C). Control mice were immunized with each of the adjuvants alone (Adj Ctl). Lung CFUs were determined at 14 dpc (n=8-10 mice/group). *$p<0.05$ (Mann-Whitney U test), versus adjuvant control; †$p<0.05$ (Kruskal-Wallis ranking test), GCP-rCpa1 versus the other four tested vaccines. No statistically significant differences in CFU data were found between the groups of mice that were vaccinated with GMP-rCpa1 or GCMP-rCpa1 compared to GMP and GCMP adjuvant alone, respectively.

FIGS. 3A-E—The purified rCpa1 protein stimulated significantly elevated frequency of IL-17A-producing CD4+ T cells compared to each of the antigen components. Assessment of IL-17A-producing CD4+ T cells was conducted by ELISPOT assays. C57BL/6 and HLA-DR4 transgenic mice were vaccinated with either GCP-rCpa1 or GCP alone. Splenocytes were separately incubated with the purified rCpa1, rAg2/Pra, Cs—Ag and rPmp1 proteins and the five synthetic peptides that contain human MHC II binding epitopes at a concentration of 200 nM. (A) SDS-PAGE separation of 2 μg of each purified rCpa1, rAg2/Pra, Cs—Ag and rPmp1 that migrated to the predicted corresponding sizes. The optical density of each lane was comparable, indicating an equal concentration of antigens could be calculated and achieved to stimulate CD4+ T cells. Representative images of IL-17A ELISPOT wells for control (B) and vaccinated (C) C57BL/6 and HLA-DR4 transgenic mice that express H2-IAb and HLA-DR4 haploid of MHC II molecules, respectively. Frequencies of responders (SFU) per 106 splenocytes to individual peptides of C57BL/6 (D) and HLA-DR4 transgenic mice (E) were plotted. *$p<0.05$ (Student t-test), GCP-rCpa1 versus Adjuvant Ctl; †$p<0.05$ (Student-Newman-Keuls test), rCpa1 versus the other seven tested constituent antigens. Data are the mean±SEM (n=4 mice/group).

FIGS. 4A-B—The GCP-rCpa1 vaccine offered protection for both C57BL/6 and HLA-DR4 transgenic mice against pulmonary *Coccidioides* infection. Survival plots were determined for groups of 10 C57BL/6 and HLA-DR4 transgenic mice (A, B) that were vaccinated with the GCP-rCpa1 vaccine or GCP alone, respectively. Mice were intranasally challenged with 80-100 *Coccidioides* spores. ($P<0.001$, Kaplan Meier survival and chi-square test). Data are representative of two independent experiments.

FIG. 5—The GCP-rCpa1-primed splenocytes secreted significantly elevated amounts of IL-17A compared to the other four rCpa1-adjuvant formulations. Concentrations of IFN-γ, IL-4 and IL-17A detected in culture supernatants of in vitro-stimulated, immune splenocytes isolated from the HLA-DR4 mice that were subcutaneously vaccinated twice with the indicated vaccine. The stimulated cells were incubated with 10 μg/ml rCpa1 protein in the culture medium. *$p<0.001$ (Student t-test), stimulated (+) versus non-stimulated (−) data; †$p<0.05$ (Student-Newman-Keuls test), GCP-rCpa1 versus the other 4 antigen-adjuvant formulations.

FIGS. 6A-E—HLA-DR4 transgenic mice vaccinated with GCP-rCpa1 acquired the highest numbers of Th17 cells into the infected lungs at 7 dpc. Flow cytometric analysis of IFN-γ- and IL-17A-expressing Th1 and Th17 cells, respectively in lungs of HLA-DR4 transgenic mice that were vaccinated with rCpa1 encapsulated in each of the tested adjuvants. Mice immunized with adjuvant alone served as controls. The percentages of gated, specific cytokine-producing cells per lung organ (insets in panel A) and the numbers (B to E) of Th1 (CD4+IFN-γ+) and Th17 (CD4+ IL-17A+) cells in the *Coccidioides*-infected lungs at 7 and 14 dpc, respectively, were determined by intracellular cytokine staining. Only presentative plots of ODN/IFA control were inserted in Panel A, but specific Th1 and Th17 cells were calculated for all five types of adjuvant controls and presented in panels B-E. *$p<0.05$ (Student t-test), versus Adjuvant Ctl; †$p<0.05$ (Student-Newman-Keuls test), GCP-rCpa1 versus the other four antigen-adjuvant formulations. Data are the mean±SEM (n=4 mice/group). The data presented are representative of 2 independent experiments.

FIGS. 7A-H—Comparison of reactogenicity of the subcutaneously administered GCP-rCpa1 and GP-rCpa1 vaccines in the injection sites of HLA-DR4 transgenic mice. Paraffin sections of skin biopsy specimens from vaccination sites that were stained with hematoxylin and eosin (10×) (A and C) or Gomori methenamine silver (B and D) showed moderate levels of inflammatory response at 2 days post vaccination. A denser layer with scattered aggregates of inflammatory cells surrounded GCPs compared to the cells only formed scattered aggregates around GPs (A, C, E and G). The corresponding areas enclosed boxes in panels A-D are shown at higher magnification in panels E-H (40×). Both mononuclear monocytes and polymorphonuclear granulocytes are visible in both hypodermis tissue injected with GCP-rCpa1 and GP-rCpa1 (E, G). White arrows in panels B and D indicate GCPs, GPs and amorphous yeast cell-wall materials. Black bars in panels A-D represent 0.5 mm, while white bars 200 µm.

FIGS. 8A-E—GCPs were better processed by macrophages and dendritic cells at the subcutaneous vaccination sites compared to GPs. Single cell preparations from the excised hypodermis tissue of mice that were vaccinated with GCP-OVAcy3 and GP-OVAcy3 were analyzed using an Amines ImageStream MKII cytometer. Numbers of DCs, MØs and PMNs were determined for CD11b+CD11c+, F4/80+Ly6G- and F4/80-Ly6G+ cells in the gated, live CD45+ leukocyte population, respectively (A). Representative images of bright field (BF), each fluorochrome channels and overlaid images (CD11b+OVAcy3, CD11c+OVAcy3, Ly6G+OVAcy3 and F4/80+ OVAcy3) of DCs, MΦs and PMNs that were positive for OVAcy3 were shown in (B). PMNs, MΦs and DCs were the most abundant phagocytes that infiltrated into the vaccination sites. Vaccine particles were engulfed by all 3 types of phagocytes. GCPs induced significantly elevated recruitment of MΦs into the vaccinated sites compared to GPs (C). Numbers of DCs, MΦs and PMNs that were positive for OVAcy3 were also significantly elevated in the sites injected with GCP-OVAcy3 compared to GP-OVAcy3 (D). The vaccine antigen was only processed in MΦs and DCs as the OVAcy3 positive areas were increased significantly in these 2 cell populations (E). The data presented are representative of 3 independent experiments. *$p<0.05$ (Student t-test).

FIGS. 9A-B—rCPA1 amino acid sequence. (A) Translated amino acid sequence of rCPA1 (SEQ ID NO:2). (B) GenBank accession numbers of rCPA1 and the three constituent antigens and amino acid sequences of the 5 human MHC II-binding peptides derived from Pep1, Amn1 and Plb antigens of *Coccidioides posadasii* isolate C735.

DETAILED DESCRIPTION

Figure 5:
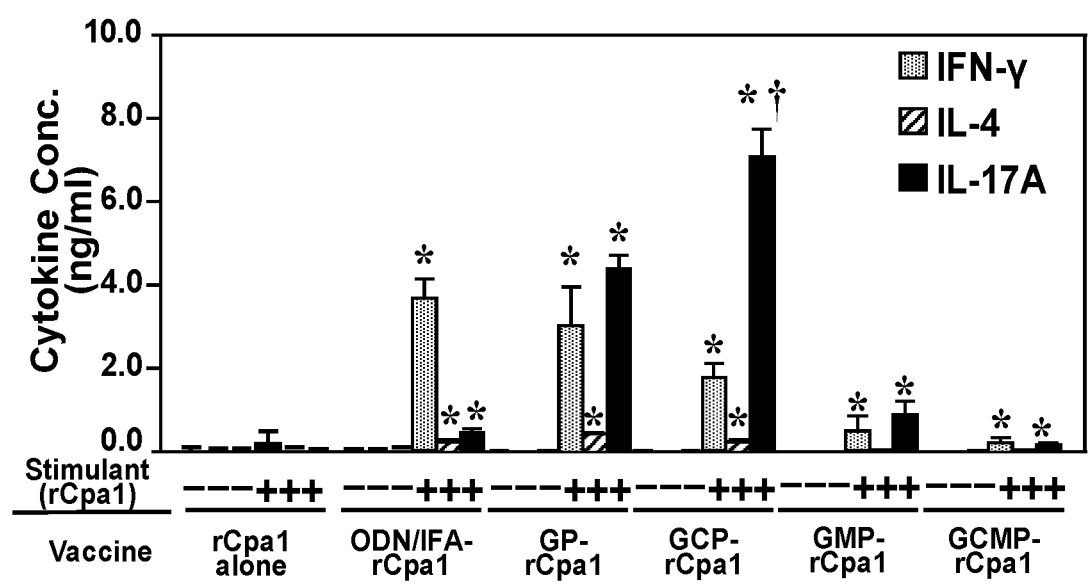

Disclosed herein is a designed and expressed multivalent, recombinant *Coccidioides* polypeptide antigen (rCpa1) that consists of fragment of Ag2/Pra, the full lengths of Cs—Ag and Pmp1, and 5 promiscuous, immunodominant T cell epitopes derived from Pep1, Amn1 and Plb of *Coccidioides posadasii* (6, 9-11, 21). Also disclosed herein is a an adjuvant/delivery system made of yeast cell-wall particles containing β-glucan and chitin that can augment Th17 immunity to improve protective efficacy of the newly created multivalent antigen (rCpa1) against *Coccidioides* infection. Specifically, the protective efficacy and immunoreactivity is disclosed herein of experimental vaccines consisting of rCpa1 encapsulated in four types of yeast cell-wall particles (GPs, GCPs, GMPs, GCMPs) and an oligonucleotide adjuvant containing 2 copies of CpG motif (ODN) that has been shown to stimulate a predominant Th1 response against *Coccidioides* infection (11, 22). The adjuvant/delivery system can encapsulate purified rCpa1 into four types of yeast cell-wall particles containing various compositions of β-glucan, mannan and chitin or mixed with an oligonucleotide (ODN) containing 2 methylated dinucleotide CpG motifs. The multivalent antigen encapsulating rCpa1 into glucan-chitin particles (GCP-rCpa1) showed a significantly elevated reduction of fungal burden for human HLA-DR4 transgenic mice compared to the other tested adjuvant-rCpa1 formulations. The rCpa1 vaccine can provide a comparable degree of survival to a live, attenuated vaccine for both genetically susceptible C57BL/6 and HLA-DR4 transgenic mice against pulmonary coccidioidomycosis.

I. *COCCIDIOIDES* ANTIGENS

A. Recombinant *Coccidioides* Antigens

Figure 1A:
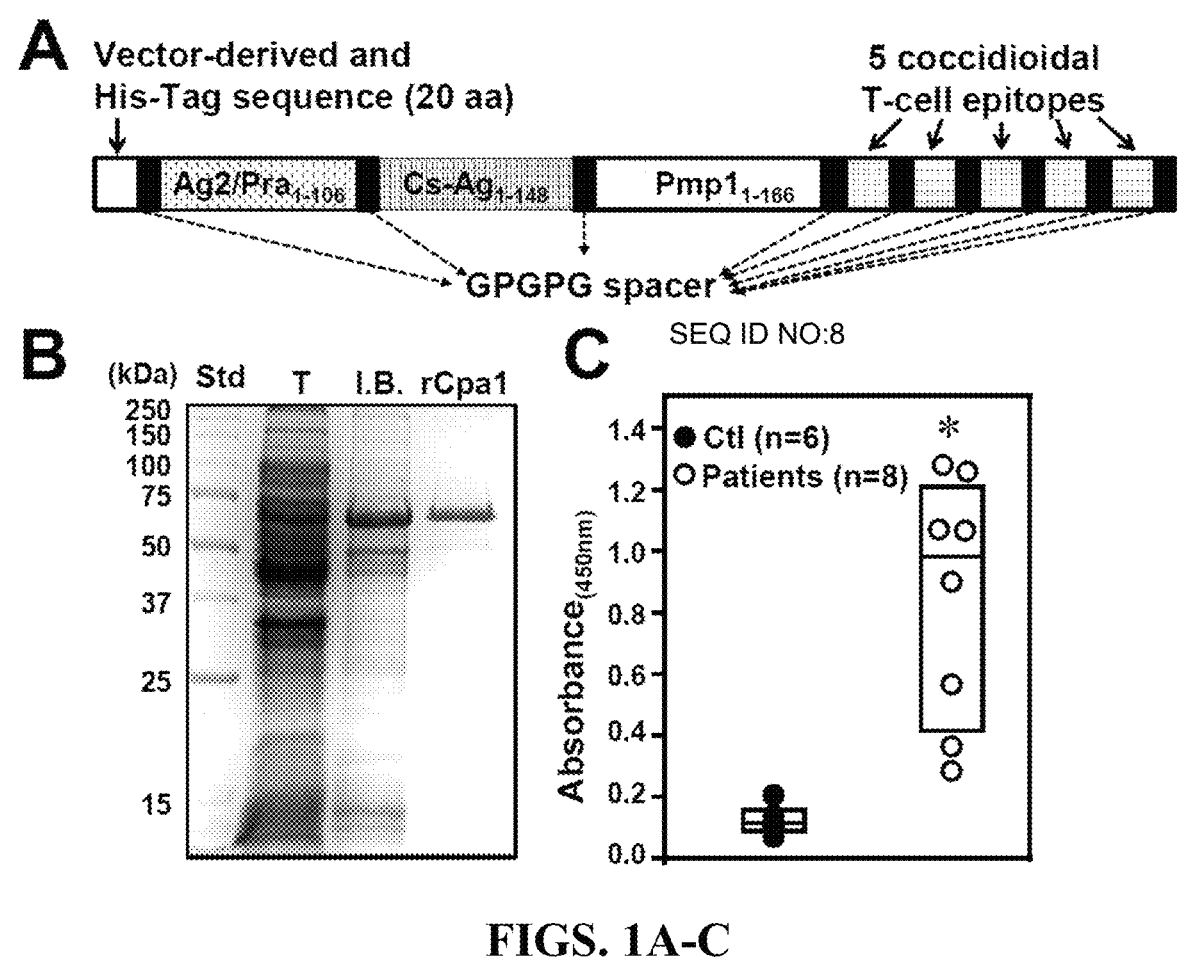

A recombinant antigen disclosed herein has the sequence of rCpa1 (SEQ. ID. NO:2) shown in SEQUENCE TABLE 2. The C terminus of each antigenic peptide of the antigen was flanked by a GPGPG spacer to avoid processing of junctional epitopes as shown in FIG. 1A (6, 23). The nucleotide sequence designed to encode the rCpa1 was codon optimized for translation by *Escherichia coli*. Moderate amounts of rCpa1 were produced in the bacterial inclusion bodies (I.B.) and observed molecular mass of the purified rCpa1 in the SDS-PAGE gel is 63 kDa (FIG. 1B). The rCpa1 was purified to greater than 95% homogeneity using a nickel-affinity chromatography, refolded and solubilized in PBS buffer. Results of amino acid sequence analysis of rCpa1 were in agreement with the translated sequence of the rCpa1 protein (SEQUENCE TABLE 2).

B. Other *Coccidioides* Antigens

Certain aspects of the invention include methods and compositions concerning proteinaceous compositions including polypeptides, peptides, or nucleic acid encoding recombinant antigen variants. These proteins may be modified by deletion, insertion, and/or substitution.

Examples of various proteins that can be used in the context of the present invention can be identified by analysis of database submissions of fungal genomes.

As used herein, a "protein" or "polypeptide" refers to a molecule comprising at least ten amino acid residues. In some embodiments, a wild-type version of a protein or polypeptide are employed, however, in many embodiments of the invention, a modified protein or polypeptide is employed to generate an immune response. The terms described above may be used interchangeably. A "modified protein" or "modified polypeptide" or a "variant" refers to a protein or polypeptide whose chemical structure, particularly its amino acid sequence, is altered with respect to the wild-type protein or polypeptide. In some embodiments, a modified/variant protein or polypeptide has at least one modified activity or function (recognizing that proteins or polypeptides may have multiple activities or functions). It is specifically contemplated that a modified/variant protein or polypeptide may be altered with respect to one activity or function yet retain a wild-type activity or function in other respects, such as immunogenicity.

In certain embodiments the size of a protein or polypeptide (wild-type or modified) may comprise, but is not limited to, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1100, 1200, 1300, 1400, 1500, 1750, 2000, 2250, 2500 amino molecules or greater, and any range derivable therein, or derivative of a corresponding amino sequence described or referenced herein. It is contemplated that polypeptides may be mutated by truncation, rendering them shorter than their corresponding wild-type form, but also they might be altered by fusing or conjugating a heterologous protein sequence with a particular function (e.g., for targeting or localization, for enhanced immunogenicity, for purification purposes, etc.).

As used herein, an "amino molecule" refers to any amino acid, amino acid derivative, or amino acid mimic known in the art. In certain embodiments, the residues of the proteinaceous molecule are sequential, without any non-amino molecule interrupting the sequence of amino molecule residues. In other embodiments, the sequence may comprise one or more non-amino molecule moieties. In particular embodiments, the sequence of residues of the proteinaceous molecule may be interrupted by one or more non-amino molecule moieties.

Accordingly, the term "proteinaceous composition" encompasses amino molecule sequences comprising at least one of the 20 common amino acids in naturally synthesized proteins, or at least one modified or unusual amino acid.

Proteinaceous compositions may be made by any technique known to those of skill in the art, including (i) the expression of proteins, polypeptides, or peptides through standard molecular biological techniques, (ii) the isolation of proteinaceous compounds from natural sources, or (iii) the chemical synthesis of proteinaceous materials. The nucleotide as well as the protein, polypeptide, and peptide sequences for various genes have been previously disclosed, and may be found in the recognized computerized databases. One such database is the National Center for Biotechnology Information's Genbank and GenPept databases (on the World Wide Web at ncbi.nlm.nih.gov/). The coding regions for these genes may be amplified and/or expressed using the techniques disclosed herein or as would be known to those of ordinary skill in the art.

Amino acid sequence variants of a recombinant antigen disclosed herein and other polypeptides of the invention can be substitutional, insertional, or deletion variants. A variation in a polypeptide of the invention may affect 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more non-contiguous or contiguous amino acids of the polypeptide, as compared to wild-type. A variant can comprise an amino acid sequence that is at least 50%, 60%, 70%, 80%, or 90%, including all values and ranges there between, identical to any sequence provided or referenced herein, e.g., a sequence of SEQUENCE TABLE NO. 1 (SEQ ID NO:2). A variant can include 2, 3, 4, 5, 6, 7, 8, 9, 10, 11, 12, 13, 14, 15, 16, 17, 18, 19, 20, or more substitute amino acids. A polypeptide of a *Coccidioides* species, such as Ag2/Pra, Pra2, Cs—Ag, Ure, Gel1, Pmp1, Pep1, Amn1, and/or Plb, are contemplated for use in compositions and methods described herein.

Deletion variants typically lack one or more residues of the native or wild-type protein. Individual residues can be deleted or a number of contiguous amino acids can be deleted. A stop codon may be introduced (by substitution or insertion) into an encoding nucleic acid sequence to generate a truncated protein. Insertional mutants typically involve the addition of material at a non-terminal point in the polypeptide. This may include the insertion of one or more residues. Terminal additions, called fusion proteins, may also be generated. These fusion proteins include multimers or concatamers of one or more peptide or polypeptide described or referenced herein.

Substitutional variants typically contain the exchange of one amino acid for another at one or more sites within the protein, and may be designed to modulate one or more properties of the polypeptide, with or without the loss of other functions or properties. Substitutions may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of the polypeptide is affected. Non-conservative changes typically involve substituting a residue with one that is chemically dissimilar, such as a polar or charged amino acid for a nonpolar or uncharged amino acid, and vice versa.

Proteins of the invention may be recombinant, or synthesized in vitro. Alternatively, a non-recombinant or recombinant protein may be isolated from fungus. It is also contemplated that a fungus containing such a variant may be implemented in compositions and methods of the invention. Consequently, a protein need not be isolated.

The term "functionally equivalent codon" is used herein to refer to codons that encode the same amino acid, such as the six codons for arginine or serine, and also refers to codons that encode biologically equivalent amino acids (see below).

Codon Table

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |

-continued

| Codon Table | | | |
|---|---|---|---|
| Amino Acids | | | Codons |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

It also will be understood that amino acid and nucleic acid sequences may include additional residues, such as additional N- or C-terminal amino acids, or 5' or 3' sequences, respectively, and yet still be essentially as set forth in one of the sequences disclosed herein, so long as the sequence meets the criteria set forth above, including the maintenance of biological protein activity (e.g., immunogenicity) where protein expression is concerned. The addition of terminal sequences particularly applies to nucleic acid sequences that may, for example, include various non-coding sequences flanking either of the 5' or 3' portions of the coding region.

The following is a discussion based upon changing of the amino acids of a protein to create a variant polypeptide or peptide. For example, certain amino acids may be substituted for other amino acids in a protein structure with or without appreciable loss of interactive binding capacity with structures such as, for example, antigen-binding regions of antibodies or binding sites on substrate molecules. Since it is the interactive capacity and nature of a protein that defines that protein's functional activity, certain amino acid substitutions can be made in a protein sequence, and in its underlying DNA coding sequence, and nevertheless produce a protein with a desirable property. It is thus contemplated by the inventors that various changes may be made in the DNA sequences of genes.

It is contemplated that in compositions of the invention, there is between about 0.001 mg and about 10 mg of total polypeptide, peptide, and/or protein per ml. The concentration of protein in a composition can be about, at least about or at most about 0.001, 0.010, 0.050, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0 mg/ml or more (or any range derivable therein). Of this, about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100% may be a recombinant antigen disclosed herein or its variant and may be used in combination with other peptides or polypeptides, such as other fugal peptides and/or antigens.

The present invention contemplates the administration of recombinant antigen disclosed herein and variants thereof to effect a preventative therapy or therapeutic effect against the development of a disease or condition associated with infection by a *Coccidioides* pathogen.

In certain aspects, combinations of *Coccidioides* antigens are used in the production of an immunogenic composition that is effective at treating or preventing *Coccidioides* infection. Different molecules on the surface of the fungus are involved in different steps of the infection cycle. Combinations of certain antigens can elicit an immune response which protects against multiple stages of *Coccidioides* infection. The effectiveness of the immune response can be measured either in animal model assays and/or using an opsonophagocytic assay.

B. Polypeptides and Polypeptide Production

The present invention describes polypeptides, peptides, and proteins and immunogenic fragments thereof for use in various embodiments of the present invention. For example, specific polypeptides are assayed for or used to elicit an immune response. In specific embodiments, all or part of the proteins of the invention can also be synthesized in solution or on a solid support in accordance with conventional techniques. Various automatic synthesizers are commercially available and can be used in accordance with known protocols.

Alternatively, recombinant DNA technology may be employed wherein a nucleotide sequence which encodes a peptide of the invention is inserted into an expression vector, transformed or transfected into an appropriate host cell and cultivated under conditions suitable for expression.

One embodiment of the invention includes the use of gene transfer to cells, including microorganisms, for the production and/or presentation of polypeptides or peptides. The gene for the polypeptide or peptide of interest may be transferred into appropriate host cells followed by culture of cells under the appropriate conditions. The generation of recombinant expression vectors, and the elements included therein, are well known in the art and briefly discussed herein. Alternatively, the protein to be produced may be an endogenous protein normally synthesized by the cell that is isolated and purified.

Another embodiment of the present invention uses autologous B lymphocyte cell lines, which are transfected with a viral vector that expresses an immunogen product, and more specifically, a protein having immunogenic activity. Other examples of mammalian host cell lines include, but are not limited to Vero and HeLa cells, other B- and T-cell lines, such as CEM, 721.221, H9, Jurkat, Raji, as well as cell lines of Chinese hamster ovary, W138, BHK, COS-7, 293, HepG2, 3T3, RIN and MDCK cells. In addition, a host cell strain may be chosen that modulates the expression of the inserted sequences, or that modifies and processes the gene product in the manner desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to ensure the correct modification and processing of the foreign protein expressed.

A number of selection systems may be used including, but not limited to HSV thymidine kinase, hypoxanthine-guanine phosphoribosyltransferase, and adenine phosphoribosyltransferase genes, in tk−, hgprt− or aprt− cells, respectively. Also, anti-metabolite resistance can be used as the basis of selection: for dhfr, which confers resistance to trimethoprim and methotrexate; gpt, which confers resistance to mycophenolic acid; neo, which confers resistance to the aminoglycoside G418; and hygro, which confers resistance to hygromycin.

Animal cells can be propagated in vitro in two modes: as non-anchorage-dependent cells growing in suspension throughout the bulk of the culture or as anchorage-dependent cells requiring attachment to a solid substrate for their propagation (i.e., a monolayer type of cell growth).

Non-anchorage dependent or suspension cultures from continuous established cell lines are the most widely used means of large scale production of cells and cell products. However, suspension cultured cells have limitations, such as tumorigenic potential and lower protein production than adherent cells.

Where a protein is specifically mentioned herein, it is preferably a reference to a native or recombinant protein or optionally a protein in which any signal sequence has been removed. The protein may be isolated directly from the *Coccidioides* species or produced by recombinant DNA techniques. Immunogenic fragments of the protein may be incorporated into the immunogenic composition of the invention. These are fragments comprising at least 10 amino acids, 20 amino acids, 30 amino acids, 40 amino acids, 50 amino acids, or 100 amino acids, including all values and ranges there between, taken contiguously from the amino acid sequence of the protein. In addition, such immunogenic fragments are immunologically reactive with antibodies generated against the *Coccidioides* proteins or with antibodies generated by infection of a mammalian host with *Coccidioides*. Immunogenic fragments also include fragments that when administered at an effective dose, (either alone or as a hapten bound to a carrier), elicit a protective or therapeutic immune response against *Coccidioides* infection, in certain aspects it is protective against *Coccidioides posadasii* and/or *Coccidioides immitis* infection. Such an immunogenic fragment may include, for example, the protein lacking an N-terminal leader sequence, and/or a transmembrane domain and/or a C-terminal anchor domain. In a preferred aspect the immunogenic fragment according to the invention comprises substantially all of the extracellular domain of a protein which has at least 80% identity, at least 85% identity, at least 90% identity, at least 95% identity, or at least 97-99% identity, including all values and ranges there between, to a sequence selected segment of a polypeptide described or referenced herein.

Also included in immunogenic compositions of the invention are fusion proteins composed of one or more *Coccidioides* proteins, or immunogenic fragments of *Coccidioides* proteins. Such fusion proteins may be made recombinantly and may comprise one portion of at least 1, 2, 3, 4, 5, or 6 *Coccidioides* proteins or segments. Alternatively, a fusion protein may comprise multiple portions of at least 1, 2, 3, 4 or 5 *Coccidioides* proteins. These may combine different *Coccidioides* proteins and/or multiples of the same protein or protein fragment, or immunogenic fragments in the same protein (forming a multimer or a concatamer). Alternatively, the invention also includes individual fusion proteins of *Coccidioides* proteins or immunogenic fragments thereof, as a fusion protein with heterologous sequences such as a provider of T-cell epitopes or purification tags, for example: β-galactosidase, glutathione-S-transferase, green fluorescent proteins (GFP), epitope tags such as FLAG, myc tag, poly histidine, or viral surface proteins such as influenza virus haemagglutinin, or bacterial proteins such as tetanus toxoid, diphtheria toxoid, or CRM197.

II. NUCLEIC ACIDS

In certain embodiments, the present invention concerns recombinant polynucleotides encoding the proteins, polypeptides, peptides of the invention. The nucleic acid sequences for Ag2/Pra, Cs—Ag, Pmp1, Pep1, Amn1, and Plb, and other proteins are included, all of which are incorporated by reference, and can be used to prepare peptides or polypeptides.

As used in this application, the term "polynucleotide" refers to a nucleic acid molecule that either is recombinant or has been isolated free of total genomic nucleic acid. Included within the term "polynucleotide" are oligonucleotides (nucleic acids of 100 residues or less in length), recombinant vectors, including, for example, plasmids, cosmids, phage, viruses, and the like. Polynucleotides include, in certain aspects, regulatory sequences, isolated substantially away from their naturally occurring genes or protein encoding sequences. Polynucleotides may be single-stranded (coding or antisense) or double-stranded, and may be RNA, DNA (genomic, cDNA or synthetic), analogs thereof, or a combination thereof. Additional coding or non-coding sequences may, but need not, be present within a polynucleotide.

In this respect, the term "gene," "polynucleotide," or "nucleic acid" is used to refer to a nucleic acid that encodes a protein, polypeptide, or peptide (including any sequences required for proper transcription, post-translational modification, or localization). As will be understood by those in the art, this term encompasses genomic sequences, expression cassettes, cDNA sequences, and smaller engineered nucleic acid segments that express, or may be adapted to express, proteins, polypeptides, domains, peptides, fusion proteins, and mutants. A nucleic acid encoding all or part of a polypeptide may contain a contiguous nucleic acid sequence of: 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1095, 1100, 1500, 2000, 2500, 3000, 3500, 4000, 4500, 5000, 5500, 6000, 6500, 7000, 7500, 8000, 9000, 10000, or more nucleotides, nucleosides, or base pairs, including all values and ranges there between, of a polynucleotide encoding one or more amino acid sequence described or referenced herein. It also is contemplated that a particular polypeptide may be encoded by nucleic acids containing variations having slightly different nucleic acid sequences but, nonetheless, encode the same or substantially similar protein (see above).

In particular embodiments, the invention concerns isolated nucleic acid segments and recombinant vectors incorporating nucleic acid sequences that encode a recombinant antigen disclosed herein or variants thereof. The term "recombinant" may be used in conjunction with a polynucleotide or polypeptide and generally refers to a polypeptide or polynucleotide produced and/or manipulated in vitro or that is a replication product of such a molecule.

In other embodiments, the invention concerns isolated nucleic acid segments and recombinant vectors incorporating nucleic acid sequences that encode a recombinant antigen disclosed herein or a variant thereof to generate an immune response in a subject. In various embodiments the nucleic acids of the invention may be used in genetic vaccines.

The nucleic acid segments used in the present invention can be combined with other nucleic acid sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant nucleic acid protocol. In some cases, a nucleic acid sequence may encode a polypeptide sequence with additional heterologous coding sequences, for example to allow for purification of the polypeptide, transport, secretion, post-translational modification, or for therapeutic benefits such as targeting or efficacy. As discussed above, a tag or other heterologous polypeptide may be added to the modified polypeptide-encoding sequence, wherein "heterologous" refers to a polypeptide that is not the same as the modified polypeptide.

In certain other embodiments, the invention concerns isolated nucleic acid segments and recombinant vectors that include within their sequence a contiguous nucleic acid sequence encoding one of the sequence of SEQUENCE TABLE NO. 1 (SEQ ID. NO:1) or any other nucleic acid sequences encoding the recombinant antigen disclosed herein or proteins incorporated herein by reference.

In certain embodiments, the present invention provides polynucleotide variants having substantial identity to the sequences disclosed herein; those comprising at least 70%, 75%, 80%, 85%, 90%, 95%, 96%, 97%, 98%, or 99% or higher sequence identity, including all values and ranges there between, compared to a polynucleotide sequence of this invention using the methods described herein (e.g., BLAST analysis using standard parameters).

The invention also contemplates the use of polynucleotides which are complementary to all the above described polynucleotides.

A. Vectors

Polypeptides of the invention may be encoded by a nucleic acid molecule comprised in a vector. The term "vector" is used to refer to a carrier nucleic acid molecule into which a heterologous nucleic acid sequence can be inserted for introduction into a cell where it can be replicated and expressed. A nucleic acid sequence can be "heterologous," which means that it is in a context foreign to the cell in which the vector is being introduced or to the nucleic acid in which is incorporated, which includes a sequence homologous to a sequence in the cell or nucleic acid but in a position within the host cell or nucleic acid where it is ordinarily not found. Vectors include DNAs, RNAs, plasmids, cosmids, viruses (bacteriophage, animal viruses, and plant viruses), and artificial chromosomes (e.g., YACs). One of skill in the art would be well equipped to construct a vector through standard recombinant techniques. In addition to encoding a recombinant antigen disclosed herein or variant thereof, the vector can encode other polypeptide sequences such as a one or more other fungal peptide, a tag, or an immunogenicity enhancing peptide. Useful vectors encoding such fusion proteins include pIN vectors, vectors encoding a stretch of histidines, and pGEX vectors, for use in generating glutathione S-transferase (GST) soluble fusion proteins for later purification and separation or cleavage.

The term "expression vector" refers to a vector containing a nucleic acid sequence coding for at least part of a gene product capable of being transcribed. In some cases, RNA molecules are then translated into a protein, polypeptide, or peptide. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described herein.

1. Promoters and Enhancers

A "promoter" is a control sequence. The promoter is typically a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and expression of that sequence. A promoter may or may not be used in conjunction with an "enhancer," which refers to a cis-acting regulatory sequence involved in the transcriptional activation of a nucleic acid sequence.

Naturally, it may be important to employ a promoter and/or enhancer that effectively directs the expression of the DNA segment in the cell type or organism chosen for expression. Those of skill in the art of molecular biology generally know the use of promoters, enhancers, and cell type combinations for protein expression. The promoters employed may be constitutive, tissue-specific, or inducible and in certain embodiments may direct high level expression of the introduced DNA segment under specified conditions, such as large-scale production of recombinant proteins or peptides.

Various elements/promoters may be employed in the context of the present invention to regulate the expression of a gene. Examples of such inducible elements, which are regions of a nucleic acid sequence that can be activated in response to a specific stimulus, include but are not limited to Immunoglobulin Heavy Chain, Immunoglobulin Light Chain, T Cell Receptor, HLA DQ α and/or DQ β, β Interferon, Interleukin-2, Interleukin-2 Receptor, MHC Class II 5, MHC Class II HLA-DRα, β-Actin, Muscle Creatine Kinase (MCK), Prealbumin (Transthyretin), Elastase I, Metallothionein (MTII), Collagenase, Albumin, α-Fetoprotein, γ-Globin, c-fos, c-Ha-Ras, Insulin, Neural Cell Adhesion Molecule (NCAM), α1-Antitrypain, H2B (TH2B) Histone, Mouse and/or Type I Collagen, Glucose-Regulated Proteins (GRP94 and GRP78), Rat Growth Hormone, Human Serum Amyloid A (SAA), Troponin I (TN I), Platelet-Derived Growth Factor (PDGF), Duchenne Muscular Dystrophy, SV40, Polyoma, Retroviruses, Papilloma Virus, Hepatitis B Virus, Human Immunodeficiency Virus, Cytomegalovirus (CMV) IE, Gibbon Ape Leukemia Virus.

The particular promoter that is employed to control the expression of peptide or protein encoding polynucleotide of the invention is not believed to be critical, so long as it is capable of expressing the polynucleotide in a targeted cell, preferably a bacterial cell. Where a human cell is targeted, it is preferable to position the polynucleotide coding region adjacent to and under the control of a promoter that is capable of being expressed in a human cell. Generally speaking, such a promoter might include either a bacterial, human or viral promoter.

In embodiments in which a vector is administered to a subject for expression of the protein, it is contemplated that a desirable promoter for use with the vector is one that is not down-regulated by cytokines or one that is strong enough that even if down-regulated, it produces an effective amount of a recombinant antigen disclosed herein for eliciting an immune response. Non-limiting examples of these are CMV IE and RSV LTR. Tissue specific promoters can be used, particularly if expression is in cells in which expression of an antigen is desirable, such as dendritic cells or macrophages. The mammalian MHC I and MHC II promoters are examples of such tissue-specific promoters.

2. Initiation Signals and Internal Ribosome Binding Sites (IRES)

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988; Macejak and Sarnow, 1991). IRES elements can be linked to heterologous open reading frames. Multiple open reading frames can be transcribed together, each separated by an IRES, creating polycistronic messages. Multiple genes can be efficiently expressed using a single promoter/enhancer to transcribe a single message (see U.S. Pat. Nos. 5,925,565 and 5,935,819, herein incorporated by reference).

3. Selectable and Screenable Markers

In certain embodiments of the invention, cells containing a nucleic acid construct of the present invention may be identified in vitro or in vivo by encoding a screenable or selectable marker in the expression vector. When transcribed and translated, a marker confers an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

B. Host Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector or expressing a heterologous gene encoded by a vector. A host cell can, and has been, used as a recipient for vectors or viruses. A host cell may be "transfected" or "transformed," which refers to a process by which exogenous nucleic acid, such as a recombinant protein-encoding sequence, is transferred or introduced into the host cell. A transformed cell includes the primary subject cell and its progeny.

Host cells may be derived from prokaryotes or eukaryotes, including bacteria, yeast cells, insect cells, and mammalian cells for replication of the vector or expression of part or all of the nucleic acid sequence(s). Numerous cell lines and cultures are available for use as a host cell, and they can be obtained through the American Type Culture Collection (ATCC), which is an organization that serves as an archive for living cultures and genetic materials (www.atcc.org).

C. Expression Systems

Numerous expression systems exist that comprise at least a part or all of the compositions discussed above. Prokaryote- and/or eukaryote-based systems can be employed to for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

In addition to the disclosed expression systems of the invention, other examples of expression systems include STRATAGENE®'s COMPLETE CONTROL™ Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

III. IMMUNE RESPONSE AND ASSAYS

As discussed above, the invention concerns evoking or inducing an immune response in a subject against a recombinant antigen or variants thereof. In one embodiment, the immune response can protect against or treat a subject having, suspected of having, or at risk of developing an infection or related disease, particularly those related to *Coccidioides*. One use of the immunogenic compositions of the invention is to prevent infections by inoculating a subject prior to entering an environment having an increased risk of infection.

A. Immunoassays

The present invention includes the implementation of serological assays to evaluate whether and to what extent an immune response is induced or evoked by compositions of the invention. There are many types of immunoassays that can be implemented. Immunoassays encompassed by the present invention include, but are not limited to, those described in U.S. Pat. No. 4,367,110 (double monoclonal antibody sandwich assay) and U.S. Pat. No. 4,452,901 (western blot). Other assays include immunoprecipitation of labeled ligands and immunocytochemistry, both in vitro and in vivo.

Immunoassays generally are binding assays. Certain preferred immunoassays are the various types of enzyme linked immunosorbent assays (ELISAs) and radioimmunoassays (RIA) known in the art. Immunohistochemical detection using tissue sections is also particularly useful. In one example, antibodies or antigens are immobilized on a selected surface, such as a well in a polystyrene microtiter plate, dipstick, or column support. Then, a test composition suspected of containing the desired antigen or antibody, such as a clinical sample, is added to the wells. After binding and washing to remove nonspecifically bound immune complexes, the bound antigen or antibody may be detected. Detection is generally achieved by the addition of another antibody, specific for the desired antigen or antibody, that is linked to a detectable label. This type of ELISA is known as a "sandwich ELISA." Detection also may be achieved by the addition of a second antibody specific for the desired antigen, followed by the addition of a third antibody that has binding affinity for the second antibody, with the third antibody being linked to a detectable label.

Competition ELISAs are also possible implementations in which test samples compete for binding with known amounts of labeled antigens or antibodies. The amount of reactive species in the unknown sample is determined by mixing the sample with the known labeled species before or during incubation with coated wells. The presence of reactive species in the sample acts to reduce the amount of labeled species available for binding to the well and thus reduces the ultimate signal. Irrespective of the format employed, ELISAs have certain features in common, such as coating, incubating or binding, washing to remove nonspecifically bound species, and detecting the bound immune complexes.

Antigen or antibodies may also be linked to a solid support, such as in the form of plate, beads, dipstick, membrane, or column matrix, and the sample to be analyzed is applied to the immobilized antigen or antibody. In coating a plate with either antigen or antibody, one will generally incubate the wells of the plate with a solution of the antigen or antibody, either overnight or for a specified period. The wells of the plate will then be washed to remove incompletely-adsorbed material. Any remaining available surfaces of the wells are then "coated" with a nonspecific protein that is antigenically neutral with regard to the test antisera. These include bovine serum albumin (BSA), casein, and solutions of milk powder. The coating allows for blocking of nonspecific adsorption sites on the immobilizing surface and thus reduces the background caused by nonspecific binding of antisera onto the surface.

B. Diagnosis of Fungal Infection

In addition to the use of proteins, polypeptides, and/or peptides, as well as antibodies binding these polypeptides, proteins, and/or peptides, to treat or prevent infection as described above, the present invention contemplates the use of these polypeptides, proteins, peptides, and/or antibodies in a variety of ways, including the detection of the presence of *Coccidioides* to diagnose an infection, whether in a patient or on medical equipment which may also become infected. In accordance with the invention, a preferred method of detecting the presence of infections involves the steps of obtaining a sample suspected of being infected by one or more *Coccidioides* species or strains, such as a sample taken from an individual, for example, from one's lung, blood, saliva, tissues, bone, muscle, cartilage, or skin. Following isolation of the sample, diagnostic assays utilizing the polypeptides, proteins, peptides, and/or antibodies of the present invention may be carried out to detect the presence of *Coccidioides*, and such assay techniques for determining such presence in a sample are well known to those skilled in the art and include methods such as radioimmunoassay, western blot analysis, and ELISA assays. In general, in accordance with the invention, a method of diagnosing an infection is contemplated wherein a sample suspected of being infected with *Coccidioides* has added to it the polypeptide, protein, peptide, antibody, or monoclonal antibody in accordance with the present invention, and *Coccidioides* are indicated by antibody binding to the polypeptides, proteins, and/or peptides, or polypeptides, proteins, and/or peptides binding to the antibodies in the sample.

Accordingly, antibodies in accordance with the invention may be used for the prevention of infection from *Coccidioides* fungus (i.e., passive immunization), for the treatment of an ongoing infection, or for use as research tools. The term "antibodies" as used herein includes monoclonal, polyclonal, chimeric, single chain, bispecific, simianized, and humanized or primatized antibodies as well as Fab fragments, such as those fragments which maintain the binding specificity of the antibodies, including the products of an Fab immunoglobulin expression library. Accordingly, the invention contemplates the use of single chains such as the variable heavy and light chains of the antibodies. Generation of any of these types of antibodies or antibody fragments is well known to those skilled in the art.

Any of the above described polypeptides, proteins, peptides, and/or antibodies may be labeled directly with a detectable label for identification and quantification of *Coccidioides* fungus. Labels for use in immunoassays are generally known to those skilled in the art and include enzymes, radioisotopes, and fluorescent, luminescent and chromogenic substances, including colored particles such as colloidal gold or latex beads. Suitable immunoassays include enzyme-linked immunosorbent assays (ELISA).

C. Protective Immunity

In some embodiments of the invention, proteinaceous compositions confer protective immunity to a subject. Protective immunity refers to a body's ability to mount a specific immune response that protects the subject from developing a particular disease or condition that involves the agent against which there is an immune response. An immunogenically effective amount is capable of conferring protective immunity to the subject.

As used herein in the specification and in the claims section that follows, the term polypeptide or peptide refer to a stretch of amino acids covalently linked there amongst via peptide bonds. Different polypeptides have different functionalities according to the present invention. While according to one aspect, a polypeptide is derived from an immunogen designed to induce an active immune response in a recipient, according to another aspect of the invention, a polypeptide is derived from an antibody which results following the elicitation of an active immune response in, for example, an animal, and which can serve to induce a passive immune response in the recipient. In both cases, however, the polypeptide is encoded by a polynucleotide according to any possible codon usage.

As used herein the phrase "immune response" or its equivalent "immunological response" refers to the development of a humoral (antibody mediated), cellular (mediated by antigen-specific T cells or their secretion products) or both humoral and cellular response directed against a protein, peptide, carbohydrate, or polypeptide of the invention in a recipient patient. Such a response can be an active response induced by administration of immunogen or a passive response induced by administration of antibody, antibody containing material, or primed T-cells. A cellular immune response is elicited by the presentation of polypeptide epitopes in association with Class I or Class II MHC molecules, to activate antigen-specific CD4 (+) T helper cells and/or CD8 (+) cytotoxic T cells. The response may also involve activation of monocytes, macrophages, NK cells, basophils, dendritic cells, astrocytes, microglia cells, eosinophils or other components of innate immunity. As used herein "active immunity" refers to any immunity conferred upon a subject by administration of an antigen.

As used herein "passive immunity" refers to any immunity conferred upon a subject without administration of an antigen to the subject. "Passive immunity" therefore includes, but is not limited to, administration of activated immune effectors including cellular mediators or protein mediators (e.g., monoclonal and/or polyclonal antibodies) of an immune response. A monoclonal or polyclonal antibody composition may be used in passive immunization for the prevention or treatment of infection by organisms that carry the antigen recognized by the antibody. An antibody composition may include antibodies that bind to a variety of antigens that may in turn be associated with various organisms. The antibody component can be a polyclonal antiserum. In certain aspects the antibody or antibodies are affinity purified from an animal or second subject that has been challenged with an antigen(s). Alternatively, an antibody mixture may be used, which is a mixture of monoclonal and/or polyclonal antibodies to antigens present in the same, related, or different microbes or organisms, such as fungus, including but not limited to *Coccidioides*.

Passive immunity may be imparted to a patient or subject by administering to the patient immunoglobulins (Ig) and/or other immune factors obtained from a donor or other non-patient source having a known immunoreactivity. In other aspects, an antigenic composition of the present invention can be administered to a subject who then acts as a source or donor for globulin, produced in response to challenge with the antigenic composition ("hyperimmune globulin"), that contains antibodies directed against *Coccidioides* or other organisms. A subject thus treated would donate plasma from which hyperimmune globulin would then be obtained, via conventional plasma-fractionation methodology, and administered to another subject in order to impart resistance against or to treat *Coccidioides* infection. Hyperimmune globulins according to the invention are particularly useful for immune-compromised individuals, for individuals undergoing invasive procedures or where time does not permit the individual to produce their own antibodies in response to vaccination. See U.S. Pat. Nos. 6,936,258, 6,770,278, 6,756,361, 5,548,066, 5,512,282, 4,338,298, and 4,748,018, each of which is incorporated herein by reference in its entirety, for exemplary methods and compositions related to passive immunity.

For purposes of this specification and the accompanying claims the terms "epitope" and "antigenic determinant" are used interchangeably to refer to a site on an antigen to which B and/or T cells respond or recognize. B-cell epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols (1996). Antibodies that recognize the same epitope can be identified in a simple immunoassay showing the ability of one antibody to block the binding of another antibody to a target antigen. T-cells recognize continuous epitopes of about nine amino acids for CD8 cells or about 13-15 amino acids for CD4 cells. T cells that recognize the epitope can be identified by in vitro assays that measure antigen-dependent proliferation, as determined by $^{3}$H-thymidine incorporation by primed T cells in response to an epitope (Burke et al., 1994), by antigen-dependent killing (cytotoxic T lymphocyte assay, Tigges et al., 1996) or by cytokine secretion.

The presence of a cell-mediated immunological response can be determined by proliferation assays (CD4 (+) T cells) or CTL (cytotoxic T lymphocyte) assays. The relative contributions of humoral and cellular responses to the protective or therapeutic effect of an immunogen can be distinguished by separately isolating IgG and T-cells from an immunized syngeneic animal and measuring protective or therapeutic effect in a second subject.

As used herein and in the claims, the terms "antibody" or "immunoglobulin" are used interchangeably and refer to any of several classes of structurally related proteins that function as part of the immune response of an animal or recipient, which proteins include IgG, IgD, IgE, IgA, IgM and related proteins.

Under normal physiological conditions antibodies are found in plasma and other body fluids and in the membrane of certain cells and are produced by lymphocytes of the type denoted B cells or their functional equivalent. Antibodies of the IgG class are made up of four polypeptide chains linked together by disulfide bonds. The four chains of intact IgG molecules are two identical heavy chains referred to as H-chains and two identical light chains referred to as L-chains.

In order to produce polyclonal antibodies, a host, such as a rabbit or goat, is immunized with the antigen or antigen fragment, generally with an adjuvant and, if necessary, coupled to a carrier. Antibodies to the antigen are subsequently collected from the sera of the host. The polyclonal antibody can be affinity purified against the antigen rendering it monospecific.

Monoclonal antibodies can be produced by hyperimmunization of an appropriate donor with the antigen or ex-vivo by use of primary cultures of splenic cells or cell lines derived from spleen (Anavi, 1998; Huston et al., 1991; Johnson et al., 1991; Mernaugh et al., 1995).

As used herein and in the claims, the phrase "an immunological portion of an antibody" includes a Fab fragment of an antibody, a Fv fragment of an antibody, a heavy chain of an antibody, a light chain of an antibody, a heterodimer consisting of a heavy chain and a light chain of an antibody, a variable fragment of a light chain of an antibody, a variable fragment of a heavy chain of an antibody, and a single chain variant of an antibody, which is also known as scFv. In addition, the term includes chimeric immunoglobulins which are the expression products of fused genes derived from different species, one of the species can be a human, in which case a chimeric immunoglobulin is said to be humanized. Typically, an immunological portion of an antibody competes with the intact antibody from which it was derived for specific binding to an antigen.

Optionally, an antibody or preferably an immunological portion of an antibody, can be chemically conjugated to, or expressed as, a fusion protein with other proteins. For purposes of this specification and the accompanying claims, all such fused proteins are included in the definition of antibodies or an immunological portion of an antibody.

As used herein the terms "immunogenic agent" or "immunogen" or "antigen" are used interchangeably to describe a molecule capable of inducing an immunological response against itself on administration to a recipient, either alone, in conjunction with an adjuvant, or presented on a display vehicle.

D. Treatment Methods

A method of the present invention includes treatment for a disease or condition caused by a *Coccidioides* pathogen. An immunogenic polypeptide of the invention can be given to induce an immune response in a person infected with *Coccidioides* or suspected of having been exposed to *Coccidioides*. Methods may be employed with respect to individuals who have tested positive for exposure to *Coccidioides* or who are deemed to be at risk for infection based on possible exposure.

In particular, the invention encompasses a method of treatment for *Coccidioides* infection. The immunogenic compositions and vaccines of the invention are advantageous to use to inoculate health care workers.

In some embodiments, the treatment is administered in the presence of adjuvants or carriers or other *Coccidioides* antigens. Furthermore, in some examples, treatment comprises administration of other agents commonly used against fungal infection, such as one or more antifungal.

The use of peptides for vaccination can require, but not necessarily, conjugation of the peptide to an immunogenic carrier protein, such as hepatitis B surface antigen, keyhole limpet hemocyanin, or bovine serum albumin. Methods for performing this conjugation are well known in the art.

IV. VACCINE AND OTHER PHARMACEUTICAL COMPOSITIONS AND ADMINISTRATION

A. Vaccines

The present invention includes methods for preventing or ameliorating *Coccidioides* infections. As such, the invention contemplates vaccines for use in both active and passive immunization embodiments. Immunogenic compositions, proposed to be suitable for use as a vaccine, may be prepared from immunogenic recombinant antigen disclosed herein, or a fragment thereof or a variant thereof. In certain aspects, antigenic material is extensively dialyzed to remove undesired small molecular weight molecules and/or lyophilized for more ready formulation into a desired vehicle.

Other options for a protein/peptide-based vaccine involve introducing nucleic acids encoding the antigen(s) as DNA vaccines. In this regard, reports described construction of recombinant vaccinia viruses expressing either 10 contiguous minimal CTL epitopes (Thomson, 1996) or a combination of B cell, cytotoxic T-lymphocyte (CTL), and T-helper (Th) epitopes from several microbes (An, 1997), and successful use of such constructs to immunize mice for priming protective immune responses. Thus, there is ample evidence in the literature for successful utilization of peptides, peptide-pulsed antigen presenting cells (APCs), and peptide-encoding constructs for efficient in vivo priming of protective immune responses. The use of nucleic acid sequences as vaccines is exemplified in U.S. Pat. Nos. 5,958,895 and 5,620,896.

The preparation of vaccines that contain polypeptide or peptide sequence(s) as active ingredients is generally well understood in the art, as exemplified by U.S. Pat. Nos. 4,608,251; 4,601,903; 4,599,231; 4,599,230; 4,596,792; and 4,578,770, all of which are incorporated herein by reference. Typically, such vaccines are prepared as injectables either as liquid solutions or suspensions: solid forms suitable for solution in or suspension in liquid prior to injection may also be prepared. The preparation may also be emulsified. The active immunogenic ingredient is often mixed with excipients that are pharmaceutically acceptable and compatible with the active ingredient. Suitable excipients are, for example, water, saline, dextrose, glycerol, ethanol, or the like and combinations thereof. In addition, if desired, the vaccine may contain amounts of auxiliary substances such as wetting or emulsifying agents, pH buffering agents, or adjuvants that enhance the effectiveness of the vaccines. In specific embodiments, vaccines are formulated with a combination of substances, as described in U.S. Pat. Nos. 6,793,923 and 6,733,754, which are incorporated herein by reference.

Vaccines may be conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkalene glycols or triglycerides: such suppositories may be formed from mixtures containing the active ingredient in the range of about 0.5% to about 10%, preferably about 1% to about 2%. Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain about 10% to about 95% of active ingredient, preferably about 25% to about 70%.

The polypeptides and polypeptide-encoding DNA constructs may be formulated into a vaccine as neutral or salt forms. Pharmaceutically-acceptable salts include the acid addition salts (formed with the free amino groups of the peptide) and those that are formed with inorganic acids such as, for example, hydrochloric or phosphoric acids, or such organic acids as acetic, oxalic, tartaric, mandelic, and the like.

Typically, vaccines are administered in a manner compatible with the dosage formulation, and in such amount as will be therapeutically effective and immunogenic. The quantity to be administered depends on the subject to be treated, including the capacity of the individual's immune system to synthesize antibodies and the degree of protection desired. Precise amounts of active ingredient required to be administered depend on the judgment of the practitioner. However, suitable dosage ranges are of the order of several hundred micrograms of active ingredient per vaccination. Suitable regimes for initial administration and booster shots are also variable, but are typified by an initial administration followed by subsequent inoculations or other administrations.

The manner of application may be varied widely. Any of the conventional methods for administration of a vaccine are applicable. These are believed to include oral application within a solid physiologically acceptable base or in a physiologically acceptable dispersion, parenterally, by injection and the like. The dosage of the vaccine will depend on the route of administration and will vary according to the size and health of the subject.

In certain instances, it will be desirable to have multiple administrations of the vaccine, e.g., 2, 3, 4, 5, 6 or more administrations. The vaccinations can be at 1, 2, 3, 4, 5, 6, 7, 8, to 5, 6, 7, 8, 9, 10, 11, 12 twelve week intervals, including all ranges there between. Periodic boosters at intervals of 1-5 years will be desirable to maintain protective levels of the antibodies. The course of the immunization may be followed by assays for antibodies against the antigens, as described in U.S. Pat. Nos. 3,791,932; 4,174,384 and 3,949,064.

1. Carriers

A given composition may vary in its immunogenicity. It is often necessary therefore to boost the host immune system, as may be achieved by coupling a peptide or polypeptide to a carrier. Exemplary and preferred carriers are keyhole limpet hemocyanin (KLH) and bovine serum albumin (BSA). Other albumins such as ovalbumin, mouse serum albumin, or rabbit serum albumin can also be used as carriers. Means for conjugating a polypeptide to a carrier protein are well known in the art and include glutaraldehyde, m-maleimidobencoyl-N-hydroxysuccinimide ester, carbodiimyde, and bis-biazotized benzidine.

2. Adjuvants

The immunogenicity of polypeptide or peptide compositions can be enhanced by the use of non-specific stimulators of the immune response, known as adjuvants. Disclosed herein is an adjuvant comprising four types of yeast cell-wall particles (GPs, GCPs, GMPs, GCMPs) and an oligonucleotide adjuvant containing 2 copies of CpG motif (ODN). This adjuvant enhanced the efficacy of the recombinant antigen disclosed herein. Additional suitable adjuvants include all acceptable immunostimulatory compounds, such as cytokines, toxins, or synthetic compositions. A number of adjuvants can be used to enhance an antibody response against a recombination antigen disclosed herein. Adjuvants can (1) trap the antigen in the body to cause a slow release; (2) attract cells involved in the immune response to the site of administration; (3) induce proliferation or activation of immune system cells; or (4) improve the spread of the antigen throughout the subject's body.

Adjuvants include, but are not limited to, oil-in-water emulsions, water-in-oil emulsions, mineral salts, polynucleotides, and natural substances. Specific adjuvants that may be used include IL-1, IL-2, IL-4, IL-7, IL-12, γ-interferon, GMCSP, BCG, aluminum salts, such as aluminum hydroxide or other aluminum compound, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM), and cell wall skeleton (CWS) in a 2% squalene/Tween 80 emulsion. MHC antigens may even be used. Others adjuvants or methods are exemplified in U.S. Pat. Nos. 6,814,971, 5,084,269, 6,656,462, each of which is incorporated herein by reference).

Various methods of achieving adjuvant affect for the vaccine includes use of agents such as aluminum hydroxide or phosphate (alum), commonly used as about 0.05 to about 0.1% solution in phosphate buffered saline, admixture with synthetic polymers of sugars (CARBOPOL®) used as an about 0.25% solution, aggregation of the protein in the vaccine by heat treatment with temperatures ranging between about 70° to about 101° C. for a 30-second to 2-minute period, respectively. Aggregation by reactivating with pepsin-treated (Fab) antibodies to albumin; mixture with bacterial cells (e.g., *C. parvum*), endotoxins or lipopolysaccharide components of Gram-negative bacteria; emulsion in physiologically acceptable oil vehicles (e.g., mannide mono-oleate (Aracel A)); or emulsion with a 20% solution of a perfluorocarbon (FLUOSOL-DA®) used as a block substitute may also be employed to produce an adjuvant effect.

Examples of and often preferred adjuvants include complete Freund's adjuvant (a non-specific stimulator of the immune response containing killed *Mycobacterium tuberculosis*), incomplete Freund's adjuvants, and aluminum hydroxide.

In some aspects, it is preferred that the adjuvant be selected to be a preferential inducer of either a Th1, a Th2 and/or Th17 type of response. High levels of Th1- and Th17-type cytokines tend to favor the induction of cell mediated immune responses to a given antigen, while high levels of Th2-type cytokines tend to favor the induction of humoral immune responses to the antigen.

The distinction of Th1, Th2, and Th17-type immune response is not absolute. In reality an individual will support an immune response which is described as being predominantly Th1, predominantly Th2 or predominantly Th17. However, it is often convenient to consider the families of cytokines in terms of that described in murine CD4+ T cell clones (O'Shea and Paul, Science 2010, 327:1098; Becattini et al., Science 2015 347:400). Traditionally, Th1-type responses are associated with the production of the INF-γ and IL-2 cytokines by T-lymphocytes. Other cytokines often directly associated with the induction of Th1-type immune responses are not produced by T-cells, such as IL-12. Th2-type responses are associated with the secretion of IL-4, IL-5, and IL-10. Furthermore, Th17-type responses are associated with the secretion of IL-17A, IL-17B, IL-17C, IL-17D, IL-17F, IL-22 and IL-23. Cytokines IL-1 and IL-6 are producted by other immune cells to guide the development of Th17-type response.

In addition to adjuvants, it may be desirable to co-administer biologic response modifiers (BRM) to enhance immune responses. BRMs have been shown to upregulate T cell immunity or downregulate suppresser cell activity. Such BRMs include, but are not limited to, Cimetidine (CIM; 1200 mg/d) (Smith/Kline, Pa.); or low-dose Cyclophosphamide (CYP; 300 mg/m$^2$) (Johnson/Mead, N.J.) and cytokines such as γ-interferon, IL-1, IL-2, IL-6, or IL-12 or genes encoding proteins involved in immune helper functions, such as B-7.

B. Lipid Components and Moieties

In certain embodiments, the present invention concerns compositions comprising one or more lipids associated with a nucleic acid or a polypeptide/peptide. A lipid is a substance that is insoluble in water and extractable with an organic solvent. Compounds other than those specifically described herein are understood by one of skill in the art as lipids, and are encompassed by the compositions and methods of the present invention. A lipid component and a non-lipid may be attached to one another, either covalently or non-covalently.

A lipid may be a naturally occurring lipid or a synthetic lipid. However, a lipid is usually a biological substance. Biological lipids are well known in the art, and include for example, neutral fats, phospholipids, phosphoglycerides, steroids, terpenes, lysolipids, glycosphingolipids, glucolipids, sulphatides, lipids with ether and ester-linked fatty acids and polymerizable lipids, and combinations thereof.

A nucleic acid molecule or a polypeptide/peptide, associated with a lipid may be dispersed in a solution containing a lipid, dissolved with a lipid, emulsified with a lipid, mixed with a lipid, combined with a lipid, covalently bonded to a lipid, contained as a suspension in a lipid or otherwise associated with a lipid. A lipid or lipid-poxvirus-associated composition of the present invention is not limited to any particular structure. For example, they may also simply be interspersed in a solution, possibly forming aggregates which are not uniform in either size or shape. In another example, they may be present in a bilayer structure, as micelles, or with a "collapsed" structure. In another non-limiting example, a lipofectamine (Gibco BRL)-poxvirus or Superfect (Qiagen)-poxvirus complex is also contemplated.

In certain embodiments, a composition may comprise about 1%, about 2%, about 3%, about 4% about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or any range there between, of a particular lipid, lipid type, or non-lipid component such as an adjuvant, antigen, peptide, polypeptide, sugar, nucleic acid or other material disclosed herein or as would be known to one of skill in the art. In a non-limiting example, a composition may comprise about 10% to about 20% neutral lipids, and about 33% to about 34% of a cerebroside, and about 1% cholesterol. In another non-limiting example, a liposome may comprise about 4% to about 12% terpenes, wherein about 1% of the micelle is specifically lycopene, leaving about 3% to about 11% of the liposome as comprising other terpenes; and about 10% to about 35% phosphatidyl choline, and about 1% of a non-lipid component. Thus, it is contemplated that compositions of the present invention may comprise any of the lipids, lipid types or other components in any combination or percentage range.

C. Combination Therapy

The compositions and related methods of the present invention, particularly administration of the recombinant antigen disclosed herein or a variant thereof, may also be used in combination with the administration of traditional therapies. These include, but are not limited to, the administration of antifungals such as fluconazole, itraconazole, amphotericin B, voriconazole, and posaconazole.

In one aspect, it is contemplated that a polypeptide vaccine and/or therapy is used in conjunction with antifungal treatment. Alternatively, the therapy may precede or follow the other agent treatment by intervals ranging from minutes to weeks. In embodiments where the other agents and/or a proteins or polynucleotides are administered separately, one would generally ensure that a significant period of time did not expire between the time of each delivery, such that the agent and antigenic composition would still be able to exert an advantageously combined effect on the subject. In such instances, it is contemplated that one may administer both modalities within about 12-24 h of each other or within about 6-12 h of each other. In some situations, it may be desirable to extend the time period for administration significantly, where several days (2, 3, 4, 5, 6 or 7) to several weeks (1, 2, 3, 4, 5, 6, 7 or 8) lapse between the respective administrations.

Various combinations may be employed, for example antifungal therapy is "A" and the immunogenic molecule given as part of an immune therapy regime, such as an antigen, is "B":

A/B/A B/A/B A/A/B B/B/A A/A/B A/B/B B/A/A A/B/B/B B/A/B/B
B/B/B/A B/B/A/B A/A/B/B A/B/A/B A/B/B/A B/B/A/A
B/A/B/A B/A/A/B A/A/A/B B/A/A/A A/B/A/A A/A/B/A

Administration of the immunogenic compositions of the present invention to a patient/subject will follow general protocols for the administration of such compounds, taking into account the toxicity, if any, of the recombinant antigen, or other compositions described herein. It is expected that the treatment cycles would be repeated as necessary. It also is contemplated that various standard therapies, such as hydration, may be applied in combination with the described therapy.

D. General Pharmaceutical Compositions

In some embodiments, pharmaceutical compositions are administered to a subject. Different aspects of the present invention involve administering an effective amount of a composition to a subject. In some embodiments of the present invention, the recombinant antigens disclosed herein may be administered to the patient to protect against infection by one or more *Coccidioides* pathogens. Alternatively, an expression vector encoding one or more such polypeptides or peptides may be given to a patient as a preventative treatment. Additionally, such compounds can be administered in combination with an antifungal. Such compositions will generally be dissolved or dispersed in a pharmaceutically acceptable carrier or aqueous medium.

In addition to the compounds formulated for parenteral administration, such as those for intravenous or intramuscular injection, other pharmaceutically acceptable forms include, e.g., tablets or other solids for oral administration; time release capsules; and any other form currently used, including creams, lotions, mouthwashes, inhalants and the like.

The active compounds of the present invention can be formulated for parenteral administration, e.g., formulated for injection via the intravenous, intramuscular, subcutaneous, or even intraperitoneal routes. The preparation of an aqueous composition that contains an additional compound or compounds that increase the expression of MHC class I or MHC II molecules will be known to those of skill in the art in light of the present disclosure. Typically, such compositions can be prepared as injectables, either as liquid solutions or suspensions; solid forms suitable for use to prepare solutions or suspensions upon the addition of a liquid prior to injection can also be prepared; and, the preparations can also be emulsified.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The proteinaceous compositions may be formulated into a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

Administration of the compositions according to the present invention will typically be via any common route. This includes, but is not limited to oral, nasal, or buccal administration. Alternatively, administration may be by orthotopic, intradermal, subcutaneous, intramuscular, intraperitoneal, intranasal, or intravenous injection. In certain embodiments, a vaccine composition may be inhaled (e.g., U.S. Pat. No. 6,651,655, which is specifically incorporated by reference). Such compositions would normally be administered as pharmaceutically acceptable compositions that include physiologically acceptable carriers, buffers or other excipients. As used herein, the term "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio. The term "pharmaceutically acceptable carrier," means a pharmaceutically acceptable material, composition or vehicle, such as a liquid or solid filler, diluent, excipient, solvent or encapsulating material, involved in carrying or transporting a chemical agent.

For parenteral administration in an aqueous solution, for example, the solution should be suitably buffered, if necessary, and the liquid diluent first rendered isotonic with sufficient saline or glucose. These particular aqueous solutions are especially suitable for intravenous, intramuscular, subcutaneous, and intraperitoneal administration. In this connection, sterile aqueous media which can be employed will be known to those of skill in the art in light of the present disclosure. For example, one dosage could be dissolved in isotonic NaCl solution and either added to hypodermoclysis fluid or injected at the proposed site of infusion, (see for example, Remington's Pharmaceutical Sciences, 1990). Some variation in dosage will necessarily occur depending on the condition of the subject. The person responsible for administration will, in any event, determine the appropriate dose for the individual subject.

An effective amount of therapeutic or prophylactic composition is determined based on the intended goal. The term "unit dose" or "dosage" refers to physically discrete units suitable for use in a subject, each unit containing a predetermined quantity of the composition calculated to produce the desired responses discussed above in association with its administration, i.e., the appropriate route and regimen. The quantity to be administered, both according to number of treatments and unit dose, depends on the protection desired.

Precise amounts of the composition also depend on the judgment of the practitioner and are peculiar to each individual. Factors affecting dose include physical and clinical state of the subject, route of administration, intended goal of treatment (alleviation of symptoms versus cure), and potency, stability, and toxicity of the particular composition.

Upon formulation, solutions will be administered in a manner compatible with the dosage formulation and in such amount as is therapeutically or prophylactically effective. The formulations are easily administered in a variety of dosage forms, such as the type of injectable solutions described above.

E. In Vitro, Ex Vivo, or In Vivo Administration

As used herein, the term in vitro administration refers to manipulations performed on cells removed from or outside of a subject, including, but not limited to cells in culture. The term ex vivo administration as referred to herein is when cells that have been manipulated in vivo are subsequently assessed in vitro. The term in vivo administration includes all manipulations performed within a subject.

In certain aspects of the present invention, the compositions may be administered either in vitro, ex vivo, or in vivo. In certain in vitro embodiments, autologous T-lymphocyte cell lines are incubated with a microbial cell of the instant invention for 24 to 48 hours or with a recombinant protein (antigen) as described herein and/or a variant thereof and/or any other composition described herein for two hours. The transduced cells can then be used for in vitro analysis, or alternatively for ex vivo administration. U.S. Pat. Nos. 4,690,915 and 5,199,942, both incorporated herein by reference, disclose methods for ex vivo manipulation of blood mononuclear cells and bone marrow cells for use in therapeutic applications.

F. Antibodies And Passive Immunization

Another aspect of the invention is a method of preparing an immunoglobulin for use in prevention or treatment of *Coccidioides* infection comprising the steps of immunizing a recipient or donor with the vaccine of the invention and isolating immunoglobulin from the recipient or donor. An immunoglobulin prepared by this method is a further aspect of the invention. A pharmaceutical composition comprising the immunoglobulin of the invention and a pharmaceutically acceptable carrier is a further aspect of the invention which could be used in the manufacture of a medicament for the treatment or prevention of *Coccidioides* disease. A method for treatment or prevention of *Coccidioides* infection comprising a step of administering to a patient an effective amount of the pharmaceutical preparation of the invention is a further aspect of the invention.

Inocula for polyclonal antibody production are typically prepared by dispersing the antigenic composition in a physiologically tolerable diluent such as saline or other adjuvants suitable for human use to form an aqueous composition. An immunostimulatory amount of inoculum is administered to a mammal and the inoculated mammal is then maintained for a time sufficient for the antigenic composition to induce protective antibodies.

The antibodies can be isolated to the extent desired by well-known techniques such as affinity chromatography (Harlow and Lane, 1988). Antibodies can include antiserum preparations from a variety of commonly used animals, e.g. goats, primates, donkeys, swine, horses, guinea pigs, rats or man.

An immunoglobulin produced in accordance with the present invention can include whole antibodies, antibody fragments or subfragments. Antibodies can be whole immunoglobulins of any class (e.g., IgG, IgM, IgA, IgD or IgE), chimeric antibodies or hybrid antibodies with dual specificity to two or more antigens of the invention. They may also be fragments (e.g., F(ab')2, Fab', Fab, Fv and the like) including hybrid fragments. An immunoglobulin also includes natural, synthetic, or genetically engineered proteins that act like an antibody by binding to specific antigens to form a complex.

A vaccine of the present invention can be administered to a recipient who then acts as a source of immunoglobulin, produced in response to challenge from the specific vaccine. A subject thus treated would donate plasma from which hyperimmune globulin would be obtained via conventional plasma fractionation methodology. The hyperimmune globulin would be administered to another subject in order to impart resistance against or treat *Coccidioides* infection. Hyperimmune globulins of the invention are particularly useful for treatment or prevention of *Coccidioides* disease in infants, immune compromised individuals, or where treatment is required and there is no time for the individual to produce antibodies in response to vaccination.

An additional aspect of the invention is a pharmaceutical composition comprising two of more monoclonal antibodies (or fragments thereof; preferably human or humanized) reactive against at least two constituents of the immunogenic composition of the invention, which could be used to treat or prevent infection by fungus, preferably *Coccidioides*, such as *Coccidioides posadasii*. Such pharmaceutical compositions comprise monoclonal antibodies that can be whole immunoglobulins of any class, chimeric antibodies, or hybrid antibodies with specificity to two or more antigens of the invention. They may also be fragments (e.g., F(ab')2, Fab', Fab, Fv and the like) including hybrid fragments.

Methods of making monoclonal antibodies are well known in the art and can include the fusion of splenocytes with myeloma cells (Kohler and Milstein, 1975; Harlow and Lane, 1988). Alternatively, monoclonal Fv fragments can be obtained by screening a suitable phage display library (Vaughan et al., 1998). Monoclonal antibodies may be humanized or part humanized by known methods.

V. EXAMPLES

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1

Protective Immune Responses Against *Coccidioides* Species

A. Results

Generation of a multivalent recombinant chimeric polypeptide antigen (rCpa1). The translated amino acid sequence of rCpa1 was deposited in GenBank (accession number: #KY883768) and will be made publicly available in GenBank after the filing of this application. The amino acid sequence of rCpa1 (SEQ ID NO:2) is also shown in SEQUENCE TABLE 2. The C terminus of each antigenic peptide was flanked by a GPGPG spacer to avoid processing of junctional epitopes as shown in FIG. 1A. The nucleotide sequence designed to encode the rCpa1 was codon optimized for translation by *Escherichia coli*. Moderate amounts of rCpa1 were produced in the bacterial inclusion bodies (I.B.) and observed molecular mass of the purified rCpa1 in the SDS-PAGE gel is 63 kDa (FIG. 1B). The rCpa1 was purified to greater than 95% homogeneity using a nickel-affinity chromatography, refolded and solubilized in PBS buffer. Results of amino acid sequence analysis of rCpa1 were in agreement with the translated sequence of the rCpa1 protein (SEQUENCE TABLE 2). We performed ELISAs to test the range of reactivity of patient sera with the purified rCpa1 protein (FIG. 1C). Sera from all 8 individual patients diagnosed with pulmonary *Coccidioides* infection reacted with the recombinant protein, and the median absorbance determined as total bound IgG-specific antibody was 0.96 compared to 0.11 for the control sera (n=6; Student t-test, p<0.001).

One example of a DNA sequence encoding rCpa1 has the following nucleic acid sequence:

```
                                            (SEQ ID NO: 1)
ATGGGCAGCAGCCATCATCATCATCATCACAGCAGCGGCCTGGTGCCGCG

CGGCAGCCATATGGGCCCGGGTCCGGGTATGCAGTTCAGCCACGCGCTGA

TCGCGCTGGTTGCAGCGGGTCTGGCTTCCGCACAGCTGCCGGACATCCCG

CCGTGCGCTCTGAACTGTTTCGTGGAGGCGCTGGGCAACGATGGTTGTAC

TCGTCTGACCGACTTTAAATGTCACTGCTCCAAACCGGAGCTGCCGGGTC

AGATTACTCCGTGCGTTGAAGAAGCGTGCCCGCTGGACGCGCGCATCTCT

GTTTCTAACATTGTTGTTGACCAGTGTTCTAAAGCGGGTGTTCCGATTGA

CATTCCGCCGGTTGATACCACTGCTGCGCCGGAACCGTCCGAAACCGGCC

CGGGTCCGGGCATGAAATTTAGCCTGCTGTCCGCTATCGCAGCGGCGGTT

TTCGTTCCGTTTACTAGCGCGACCCCGCTGGCATCTACCGCGGACCTGTC

TTACGACACCCACTACGACGATCCGTCTCTGCCGCTGTCTGGCGTTACTT

GCTCTGATGGTGACAACGGTATGATCACCAAAGGTTACAACACCGCGGGT

GAGATTCCGAACTACCCGCACGTTGGTGGTGCATTCACCGTGGAAACCTG

GAACTCTCCGAACTGCGGTAAATGCTATAAAGTGACTTACAACGCTAAGA

CCATCTTCCTGACTGCGATCGACCACTCTAACTCTGGTTTCAACATCGCG

AAAAAATCTATGGACGTTCTGACTAACGGTCGTGCAGAAGAACTGGGCCG

TATCAAAGTTACCTACGAGGAAGTTGCATCCTCCCTGTGTGGTCTGAAAG
```

-continued
```
GCCCGGGTCCGGGCATGGCATCCCTGAAGGCAGGCGATTCTTTCCCGTCT

GATGTTGTTTTTCTTATATTCCGTGGACCCCGGACAACAAAGACATCAA

AGCGTGTGGTATGCCGCAGAACTACGAAGCGTCTAAACTGTGGCGGACA

AAAAAGTTGTGCTGTTTTCCCTGCCGGGTGCGTTTACCCCGACCTGCTCT

GCGTCTCATCTGCCGGGTTACATTCAGAAACTGCCGCAGCTGAAGGAAAA

AGGTGTTGACGTTGTTGCGGTTCTGGCATTCAACGACGCGTGGGTTATGT

CTGCGTGGGGTAAGGCGAACGGTGTTACTGGTGACGACATCCTGTTCCTG

TCCGATCCGGAAGCGAAATTCTCTAAATCCATTGGTTGGAACGCAGGTGA

ACGTACCGGTCGTTATGCGATGATTATTGATCATGGTCAGGTGACCTACG

CGGAAATCGAACCGGGTCGTGAAGTGACCGTGTCCGGTGCTGATGCTGTG

ATTTCTAAGCTGGGCCCGGGTCCGGGCATGCGCAACTCTATCCTGCTGGC

AGCTACCGTGCTGCTGGGTTGCACTTCTGCGAAGGTTCATGGCCCGGGTC

CGGGTCACGTTCGTGCTCTGGGCCAGAAAT synthetic peptides that contain human epitopes (FIGS. 3C and 3D). In contrast, splenocytes isolated from the vaccinated HLA-DR4 mice responded to the human epitopes, P1, P2, and P10 in addition to rAg2/Prp and rPmp1 (FIGS. 3C and 3E). These data indicate that rCpa1 could enable the induction of larger repertoires of CD4+ T cells compared to each subunit peptides.

The GCP-rCpa1 vaccine offered protection for both C57BL/6 and HLA-DR4 transgenic mice. Both strains of mice were vaccinated twice with GCP-rCpa1 via subcutaneous route as described above and evaluated for survival for a period of 50 days after an intranasal challenge with a potentially lethal dose of *Coccidioides* spores (~100 spores). Mice immunized with GCP alone served as controls. All (100%) and 60% of vaccinated C57BL/6 and HLA-DR4 mice survived for a period of 50 dpc, respectively, while the control mice succumbed to coccidioidomycosis between 12-30 dpc (FIGS. 4A and 4B). Vaccinated C57BL/6 mice showed a trend of better survival with increased survival days near statistical significance (Kaplan-Meier survival analysis and Chi-squared test, P=0.053) compared to HLA-DR4 mice. Protective efficacy of GCP-rCpa1 vaccine for C57BL/6 and HLA-DR4 mice were comparable to our previously reported ΔT live attenuated vaccine against pulmonary coccidioidomycosis.

GCP adjuvant enhanced Th17 response that was associated with vaccine protection. We employed a recall response assay to determine whether immune CD4+ T cells isolated from splenocytes obtained from HLA-DR4 mice vaccinated with rCpa1 plus each of the five tested adjuvants secreted elevated amounts of IFN-γ, IL-4 and IL-17A compared to splenocytes isolated from the control mice (FIG. 5). Control CD4+ T cells isolated from mice immunized with rCpa1 without an adjuvant and each adjuvant alone secreted comparably low amounts of these cytokines after exposure to rCpa1 and culture medium (FIG. 5). CD4+ T cells isolated from mice that were vaccinated with rCpa1 formulated with ODN/IFA, GP and GCP produced comparable amounts of IFN-γ, while the GCP-rCpa1-primed CD4+ T cells secreted the highest amounts of IL-17A among these three vaccination groups upon restimulation with rCpa1 (FIG. 5).

Figure 6A:
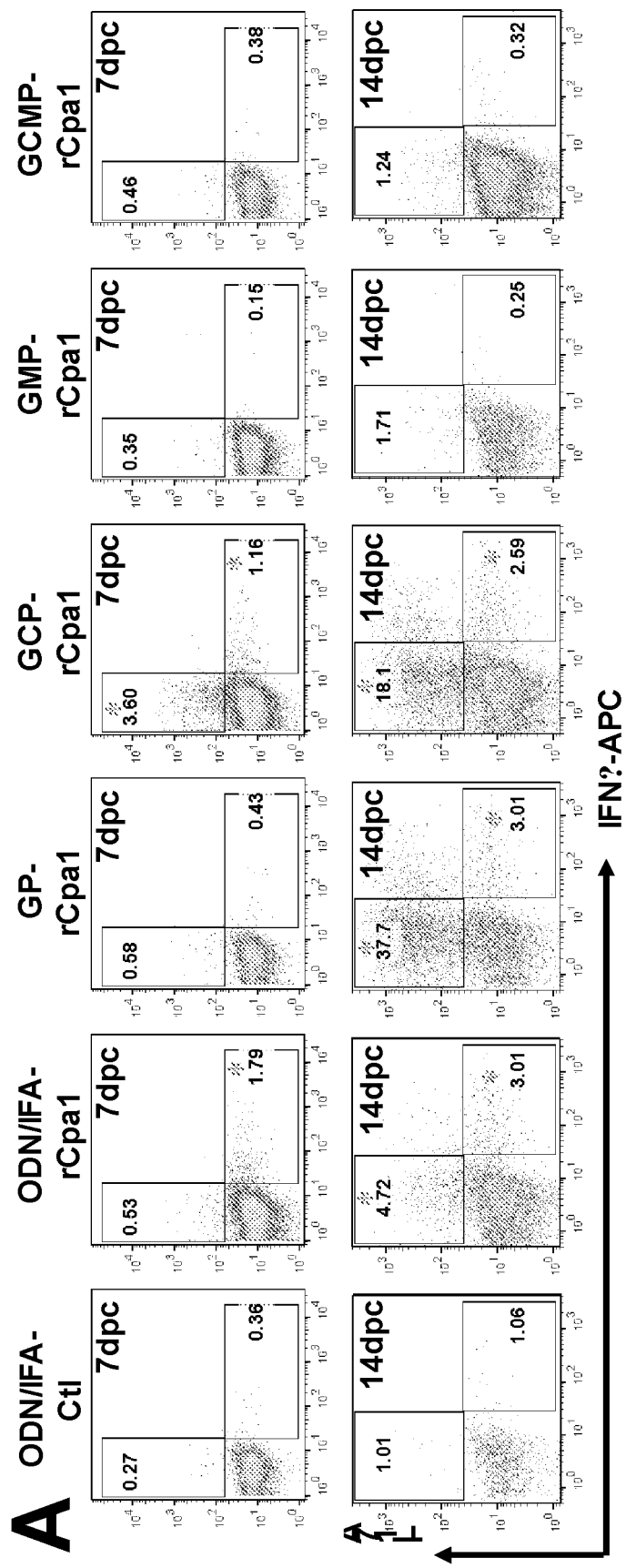

Next we determined numbers of IFN-γ- and IL-17A-producing CD4+ T cells that had infiltrated into the lungs of the vaccinated and control mice at 7 and 14 days postchallenge. The gating strategy for pulmonary Th1 and Th17 cells were CD4+CD8-IFN-γ+ and CD4+CD8-IL-17A+, respectively. Percentage and total numbers of Th1 cells were significantly increased in the lungs of mice that were vaccinated with GCP-rCpa1 and ODN/IFA-rCpa1 at 7 dpc compared to the respective adjuvant controls (FIG. 6A upper panels and 6B). Interestingly, percentages and total numbers of Th17 cells were significantly increased only in the group of mice that were vaccinated with GCP-rCpa1 at 7 dpc (FIG. 6A upper panels and 6C). At 14 dpc mice that were vaccinated with ODN/IFA-rCpa1, GP-rCpa1 and GCP-rCpa1 showed significant increases of Th1 and Th17 cells (FIG. 6A lower panels, 6D and 6E). Notably, mice that were vaccinated with GP-rCpa1 showed the highest numbers of both Th1 and Th17 cells in the lungs at 14 dpc compared to the rest of vaccination groups (FIGS. 6D and 6E), indicating a delayed T-cell response that was reported to be associated with chronic *Coccidioides* infection. In contrast, Th1 and Th17 cells were not recruited to the lungs of mice that were vaccinated with GMP-rCpa1 and GCMP-rCpa1. Concurringly, these two vaccines did not provide significant protection against pulmonary *Coccidioides* infection (FIG. 2). Taken together, these results indicated that GCP-rCpa1 stimulated robust activation of CD4+ T cells, especially Th17 cells in the lungs during early stage of *Coccidioides* infection that was correlated with significant reduction of fungal burdens.

GCP adjuvant elicited elevated infiltration of macrophages to engulf and process the vaccine at the vaccination sites compared to GPs. GCPs and GPs appear to be the two most effective adjuvants in stimulating vaccine-induced Th17 response. We further compared adjuvanticity of GCPs and GPs using comparative histopathology and imaging flow cytometry analysis of hypodermis tissue obtained from the s.c. injection sites. Mice that were vaccinated with GCP-rCpa1 and GP-rCpa1 showed minimal swelling and erythema at the injection sites at 2 days after injection. Coarsely visual examination revealed that the swelling could last for 3-6 days. Histopathological analysis of the skin biopsy showed scattered aggregates of both types of vaccine particles that were visible in the centers of the hypodermis tissues and within a dense layer of inflammatory cells (FIG. 7A-H). Notably, the infiltrated inflammatory cells formed a denser layer surrounding GCP-rCpa1 compared to GP-rCpa1 (A and C). Neutrophils (PMNs), macrophages (Møs) and dendritic cells (DCs) were visible in these vaccinated hypodermis areas (FIGS. E and G). We further characterized infiltrated inflammatory cells in hypodermis tissue obtained at 2 days post injection with Cy3-labeled ovalbumin (OVACy3) encapsulated in GCPs and GPs using a gating strategy as shown (FIG. 8A). Both GCPs and GPs were readily engulfed by PMNs, Møs and DCs that were the major infiltrating inflammatory cells in the injection sites (FIGS. 8B and C). GCPs stimulated elevated numbers of macrophages into the hypodermis tissue compared to GPs (FIG. 8C). Numbers of PMNs, Møs and DCs that were positive for OVAcy3 were significantly increased in the sites that were injected with the antigen encapsulated in GCPs compared to GPs (FIG. 8D). Subsequent proteolytic degradation of encapsulated antigens was evidenced by the increased sizes of OVAcy3 areas in DCs and Møs, but not in PMNs (FIGS. 8B and E). These results suggest that GCPs were better engulfed and processed by macrophages and dendritic cells that could lead to enhanced Th17 response compared to GPs.

Describe herein is a newly created *Coccidioides* vaccine consisting of a recombinant multivalent antigen (rCpa1) that is loaded into yeast glucan-chitin particles (GCP) to enhance Th17 immunity. Results of vaccination reveal that augmented Th17 immunity is associated with improved protective efficacy for mice. The GCP-rCpa1 formulation is the first recombinant subunit vaccine that can offer 100% and 60% survival of a period of 50 days for C57BL/6 and the highly susceptible HLA-DR4 transgenic mice, respectively. The protective efficacy of the GCP-rCpa1 vaccine is comparable to the live, attenuated (ΔT) vaccine that we have previously reported. Efforts to develop a vaccine against coccidioidomycosis started in the 1960s, where formalin-killed spherules (FKS) was the lead vaccine candidate. FKS vaccine confers protection for genetically susceptible C57BL/6 and BALB/c mice and monkeys against a potentially lethal infection with *Coccidioides*. However, a double-blinded clinical Phase III study conducted in 1980-1983 revealed that the FKS vaccine only provided a slight but statistically insignificant reduction of coccidioidomycosis incidence in the vaccinated group compared to the placebo population. FKS injection caused significant local irritation in 75% of recipients and flu-like symptom in 12% participants that might contribute to the failure of vaccination and limitation of its potential use as a human vaccine. Subsequently, several live attenuated vaccines have been created for preventive measures against pulmonary coccidioidomycosis. These cellular vaccines include a temperature sensitive mutant created by UV irradiation and two genetically engineered mutants lacking the expression of two chitinases (ΔT) and a mutant deficient in expression of an acyl-CoA ligase-like protein (ΔCps1), respectively. Despite the apparent ability of live, attenuated vaccines to elicit a highly protective immunity in mice, they may not be safe for individuals with underlying conditions of compromised cell-mediated immune systems.

The generation of recombinant antigens is an alternative strategy for the design of a clinically acceptable *Coccidioides* vaccine. The majority of protective antigens that have been characterized to date include Ag2/Pra, Pra2, Cs—Ag, Ure, Gel1, Pmp1, Pep1, Amn1 and Plb that are expressed in *Coccidioides* parasitic cells. Additionally, potential antigenic epitopes can also be identified in silico, since the genome sequences of both *Coccidioides posadasii* and *Coccidioides immitis* are available. The newly created rCpa1 contains the most immunogenic fragment of Ag2/Pra, Cs—Ag, Pmp1 and 5 peptides derived from Pep1, Amn1 and Plb that contain human epitopes. These antigens were selected because they are expressed at maximum levels during different stages of the parasitic cycle. In vivo *Coccidioides* spores grow isotropically and develop into large, multinucleate parasitic cells (spherules; >80 μm diam.). The latter undergo a process of segmentation of their cytoplasm followed by differentiation of a multitude of endospores (approx. 200-300) which are still contained within the intact spherule wall. Endospores (2-10 μm diameter) are finally released when they enlarge and cause the spherule wall to rupture. Endospore release is essential for lymphogenous or hematogenous dissemination of the pathogen within tissues of the host. The constituent antigens, Ag2/Pra, Cs—Ag and Pmp1 are differentially upregulated during the parasitic life cycle. Ag2/Pra is most abundant on mature spherules, while Cs—Ag is highly expressed on endospores (unpublished data). PLB and AMN1 transcription occurs during initiation of the parasitic cycle, while the PEP1 gene is expressed constitutively. We include vaccine antigens expressed during initial spherule formation to ensure activation of the host immune response to Coccidioidal infection in vaccinated mice prior to metastasis (endosporulation) of the pathogen. Furthermore, inclusion of additional immunogenic antigens which are produced during spherule rupture and endospore release may further enhance protection. The 5 peptides containing human epitopes were selected for incorporation into the rCpa1 multivalent antigen based upon the following criteria: (i) computational prediction of promiscuous binding to the human MHC II receptor, (ii) demonstration of the ability to be processed by antigen-presenting cells and presented to CD4+ T cells and (iii) the ability to bind with high affinity to human MHC II molecules. We suggest the rCpa1 is a multivalent antigen that can elicit a broad spectrum of CD4+ T cells that recognize antigens expressed on different developing stages of *Coccidioides* parasitic cells.

Indeed, the inventors have confirmed that the multivalent *Coccidioides* antigens can stimulate higher frequencies of Th17 cells than the single recombinant protein vaccines (FIG. 3). Compelling evidence suggests that the multivalent vaccines are more potent against pulmonary *Coccidioides* infection than a single peptide vaccine. Experimental vaccines consisting of a recombinant epitope-based vaccine (rEBV) that contain only the 5 previously identified human epitopes mixed with various adjuvants including GPs, ODN/IFA or the combination are not able to provide protection for C57BL/6 mice against pulmonary *Coccidioides* infection. The protective efficacy of rCpa1 has not been directly compared to Ag2/Pra, Cs—Ag and Pmp1, yet this antigen appear to be superior to rEBV, which only prolongs survival for an additional 2 days. The newly created GCP-rCpa1 vaccine confers protection for vaccinated HLA-DR4 transgenic and C57BL/6 mice at 60% and 100% survival for a period of 50 days, respectively. This protective efficacy is comparable to FKS and the live, attenuated ΔT vaccine that we have previously created.

The inventors found that enhancement of Th17-mediated immunity by glucan-chitin particles is associated with improved vaccine protection against pulmonary *Coccidioides* infection. Upon in vitro stimulation with the autologous antigen, immune T cells isolated from mice vaccinated with GCP-rCpa1 secrete comparable levels of IFN-γ but much higher IL-17A amount compared to GP-rCAP1 primed T cells. Similarly, mice vaccinated with GCP-rCpa1 recruit higher levels of Th17 cells during the first 7 days postchallenge and contain lower fungal burdens in the *Coccidioides*-infected lungs compared to mice vaccinated with GP-rCpa1. These data suggest that GCPs can stimulate a Th17-biased immunity that contributes to protective efficacy. Chitin is covalently bound to 13-(1, 3)-glucans in the yeast cell wall. GPs contain 80-85% β-glucan, 2-4% chitin and less than 1% mannan, while GCPs are composed of ~50-60% glucan, 20-30% chitin and less than 1% mannan. Chitin is the major polysaccharide component that is different between GPs and GCPs. While β-glucan is known as the ligand for Dectin-1, recent studies propose several potential chitin recognition receptors of mice including Toll-like receptor 2 (TLR2), fibrinogen C domain-containing protein 1 (FIBCD1) and mannose receptor that are activated by chitin fragments isolated from shrimp shells, *Aspergillus fumigatus* and *Candida albicans*, respectively. Shrimp chitin is described to have pro-inflammatory properties by inducing IL-17 via the TLR2 signaling in murine cells. A recent study reveals that recognition of *Aspergillus* chitin via the mannose receptor on the surface of the phagocytes and by the nucleotide-binding oligomerization domain 2 (NOD2) and TLR9 receptors in the cytoplasm, leading to the induction of the anti-inflammatory cytokine IL-10 in mouse macrophages. It is speculated that differences in the chitin content or polymer length may account for the observed divergence in immune stimulation properties, driving induction of anti- and pro-inflammatory cytokines. We suggest that GCPs may interact with Dectin-1 and other pattern recognition receptors that synergistically act to activate Th17 immunity. Studies are underway to investigate the mechanisms of Th17 stimulation properties of the GCP adjuvant/delivery system.

A. Materials and Methods

Fungal strain, growth conditions, and spore preparation. *Coccidioides posadasii* (C735), a virulent clinical isolate was used in this study. The saprobic phase was grown on GYE agar (1% glucose, 0.5% yeast extract, 1.5% agar) to produce spores as previously reported. All culturing and preparatory procedures, which involved live cells of *C. posadasii*, were conducted in a biosafety level 3 (BSL3) laboratory located at the University of Texas at San Antonio (UTSA).

Mouse strains. C57BL/6 mice of 8-10 weeks old were purchased from Charles River Laboratory. A breeding colony of HLA-DR4 (DRB1*0401) transgenic mice which express human MHC class II molecules was used in this study. The HLA-DR4 mice were genetically engineered from a C57BL/6 background and were backcrossed to MHC class II-deficient mice lacking IA and IE alleles to eliminate production of endogenous murine MHC class II molecules. All mice were housed in a pathogen-free animal facility at UTSA and were handled according to the guidelines of the Institutional Animal Care and Use Committee. Mice were transported to the animal BLS3 (ABSL3) laboratory before challenge with live *Coccidioides* spores.

Design, expression, and purification of the rCpa1 vaccine. A single, bacterial-expressed, recombinant *Coccidioides* polypeptide (rCpa1) was designed to contain the most immunogenic fragment of Ag2/Pra (aa #1-106; GenBank #XM_003069107), the full lengths of Cs—Ag (GenBank #XM_003056932) and Pmp1 (GenBank #XM_003069228) and the 5 most promiscuous, immunodominant T cell epitopes derived from Pep1, Amn1, and Plb. The N terminus of each antigen and epitope was flanked by a GPGPG spacer to avoid processing of junctional epitopes. The upstream 20-residue segment of the protein construct is a component of the translated plasmid expression vector (pET28b; Novagen) and includes 6 histidine residues used for nickel-affinity chromatographic purification of the rCpa1. The nucleotide sequence designed to encode the rCpa1 was codon optimized for translation by *Escherichia coli* and was synthesized by BioMatik. The synthetic 1701 bp included a stop codon and two restriction sites (NdeI and XhoI) engineered to permit the gene to be ligated into the *E. coli* expression vector in the correct translation frame. The rCpa1 was purified under denaturing conditions as previously described. Confirmation of the correct amino acid sequence of rCpa1 was performed by the Biomarker core facility at UTSA. ELISAs of the purified rCpa1 protein were conducted as previously described. Sera from patients with coccidioidomycosis and from healthy controls were tested for total IgG antibody reactivity with the purified rCpa1 protein. Patient sera (n=8) were kindly provided by Dr. Craig Rundbaken (Valley Fever Clinic, Phoenix, Ariz.). Control sera (n=6) were obtained from Innovative Research, Inc.

Vaccine preparations. Synthesized ODN (Integrated DNA Technologies, Inc.; 10 μg) was solubilized in 100 μl PBS together with 10 μg rCpa1, 25 μg MSA and mixed with 100 μl of incomplete Freund's adjuvant (Sigma) for each immunization as previously described. Yeast cell-well particles derived from *Saccharomyces cerevisiae* (GPs and GMPs) and *Rhodotorula mucilaginosa* (GCPs and GCMPs) were prepared as previously reported. Each dose of vaccine contained 10 μg rCpa1, 200 μg yeast tRNA and 25 μg mouse serum albumin (MSA) as a trapping matrix loaded into 400 μg of GPs, GCPs, GMPs or GCMPs. Confirmation of the successful incorporation of rCpa1 into the various types of yeast cell wall particles was conducted by SDS-PAGE followed by Western blot analysis with an anti-His-Tag antibody.

Vaccination protocol, animal challenge, and evaluation of protection. HLA-DR4 transgenic and C57BL/6 mice were subcutaneously immunized twice in the abdominal region at a 2-week interval. Mice were challenged intranasally with a suspension of 30 to 100 viable spores of *C. posadasii* in 35 μl of PBS 4 weeks after completion of the immunization protocol as previously reported. Mice received a corresponding adjuvant containing 200 μg yeast tRNA and 25 μg MSA were used as non-vaccination controls. Mice were sacrificed at 14 days postchallenge for determination of the fungal burden in their lungs and spleen as previously described. Survival studies of vaccinated versus non-vaccinated mice were conducted over 50 days postchallenge as previously reported.

IL-17A ELISPOT and cytokine ELISAs. Evaluation of T-cell reactivity was conducted by IL-17A ELISPOT assays essentially as reported. At 14 days post the 2nd vaccination, spleens of vaccinated or control HLA-DR4 mice were separately harvested, pooled, and macerated for isolation of immune splenocytes and CD4+ T cells as previously reported. The bacterial-expressed rAg2/Pra, native CS-Ag and rPmp1 were purified as previously described. Purities and concentrations of all three purified antigens described above along with the purified rCpa1 were analyzed by SDS-PAGE analysis. T lymphocytes were tested for an in vitro recall response to the 4 purified antigens and 5 synthetic peptides at a concentration of 200 nM. Cytokine assays was conducted by incubation of the immune and control splenocytes with 10 μg/ml rCpa1 for 48 h at 37° C. in the presence of 5% CO2, respectively. Splenocytes incubated in growth medium alone served as negative controls. After incubation, a cocktail of protease inhibitors (EDTA-free; Roche) was added to each well and culture supernatants were collected from the centrifuged samples (11,950× g, 10 min at 4° C.). The concentration of selected cytokines was determined using a Bio-Plex suspension array system (Bio-Rad) according to the manufacturer's instructions.

FACS analysis. Total pulmonary leukocytes were isolated from vaccinated and control HLA-DR4 mice at 7 and 14 days postchallenge (4 mice per group) as previously reported. A standard flow cytometry methodology was employed for direct monoclonal antibody (mAb) labeling and enumeration of selected pulmonary immune T cell phenotypes using a FACSCalibur cytometer as previously described. Permeabilized leukocytes were stained with a cocktail of fluorochrome-conjugated antibodies for IFN-γ, IL-17A, CD4 and CD8 molecules. Data was analyzed using FlowJo software version 10.

Histopathology. Comparative histopathology analysis was conducted with excised tissue from the subcutaneous vaccination sites at 2 days post infection as previously reported. Tissue sections were stained with hematoxylin and eosin (H&E) and Grocott-Gomori's methenamine sliver stain (GMS) by standard procedures. Paraffin sections were examined using a Leica DMI6000 microscope equipped with an automated TurboScan stage (Objective Imaging, Ltd.). Microscope images of tissue were acquired and analyzed using Surveyor software (Objective Imaging) as previously reported.

Imaging flow cytometry analysis. Mice were subcutaneously vaccinated with 400 μg of GCPs or GPs containing Cy3-labeled ovalbumin (OVAcy3), 200 μg yeast tRNA and 25 μg MSA on their abdomen regions. Hypodermis tissue was excised at 2 days post vaccination and single cells were prepared and stained with fluorochrome-labeled antibodies against F4/80, CD11b, CD11c, Ly6G as previously described. Following staining cells were analyzed with an ImageStreamX MKII cytometer (Millipore) with 60× objective lens at low flow rate and high sensitivity using INSPIRE software. Immune phenotyping and phagocytosis of vaccine particles were analyzed using IDEAS® software version 6.2 (Millipore).

Statistical analyses. Student t-test was used to analyze results between two treatment groups for cytokine ELISA, ELISPOT assays, cytokine concentrations, calculations of cell numbers of lung-infiltrated immune cells and percentages of specific cytokine-producing T cells, while Student-Newman-Keuls test, a type of ANOVA statistical analysis for multiple comparisons of three or above independently treated groups was used as previously reported. The differences in fungal burdens (CFUs) between two groups were analyzed by the Mann-Whitney U ranking test. When comparing fungal burdens among three and more groups of mice the Kruskal-Wallis test, a non-parametric ranking method was used as previously reported. Survival data were examined by the Kaplan-Meier test using log-rank analysis to compare survival plots as reported previously. A p value of equal or less than 0.05 was considered statistically significant.

Example 2

Figure 10:
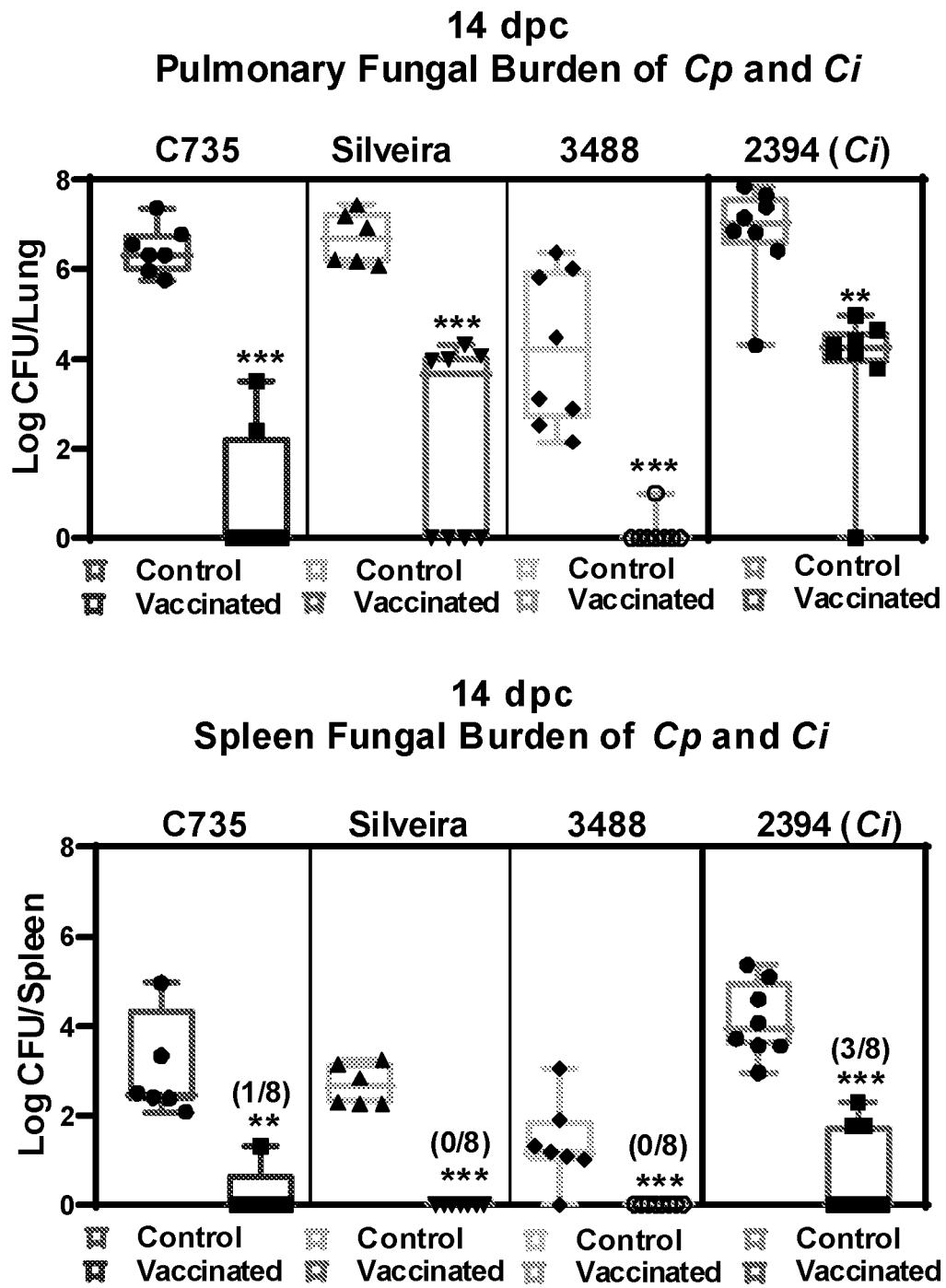
FIG. 10. Cross protection of GCP-rCPA1 vaccination against *Coccidioides* spp. Group of C57BL/6 mice were subcutaneously vaccinated with GCP-rCPA1 or GCP alone as control and intranasally challenged with 90 CFU of *C. posadasii* (C735, Silveira, 3488) or *C. immitis* (2394) isolates. Fungal burdens in the lungs and spleen were enumerated at 14 days post challenge.
Figure 11:
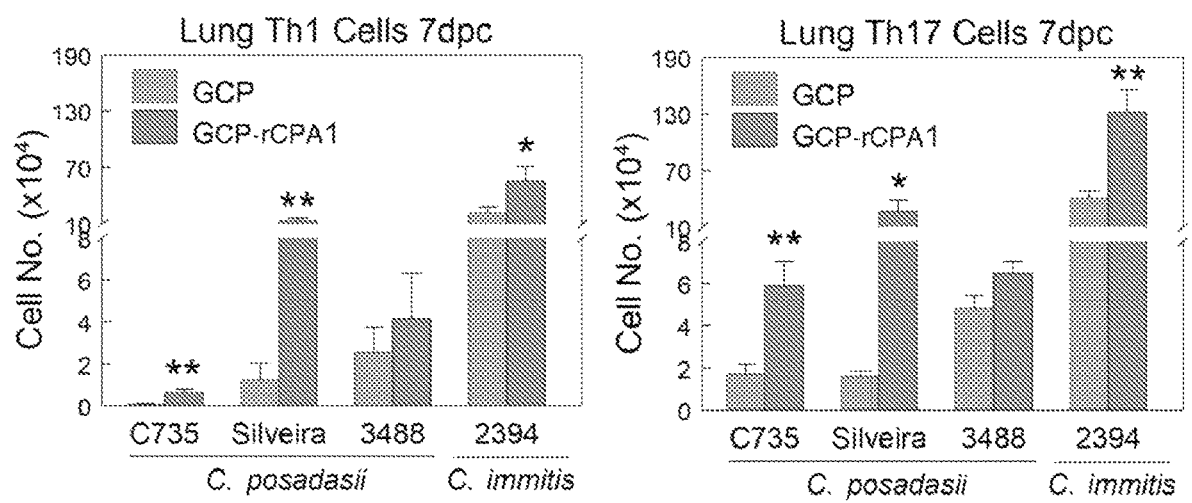
FIG. 11. rCPA1 vaccination induces protective immunity. GCP-rCPA1 vaccination induced robust Th1 and Th17 immune responses in the lungs at day 7 post pulmonary *C. posadasii* (C735, Silveira and 3488) and *C. immitis* (2394) challenge.

Cross Protection of rCPA1 Against *Coccidioides* spp.
A. Results
rCPA1 is a multivalent vaccine consisting of 6 antigens derived from *C. posadasii* C735 isolate. We PCR amplified these antigen coding sequences from 39 *C. posadasii* and 17 *C. immitis* clinical isolates. DNA sequences of these PCR amplicons were determinate and the translated amino acid sequences were aligned to identify substituted amino acid residues. We found that all antigens are conserved amongst intra-species isolates. However, inter-species comparison revealed the difference in 7 out of the total 586 amino acids within rCPA1 (Table 1). In spite of this difference, Vaccination of mice with GCP-rCPA1 provides protection against both *C. posadasii* and *C. immitis*. Specifically, we vaccinated C57BL/6 mice with GCP-rCPA1 or GCP alone as control and challenged these mice with 3 *C. posadasii* isolates (C735, Silveria, 3844) and a *C. immitis* (2394). In all 4 coccidioidal pulmonary challenge cases, mice received 3 doses of GCP-rCPA vaccine had significantly lower fungal burden in the lungs compared with GCP mock vaccination (FIG. 10). The GCP-rCPA1 vaccination also greatly reduced fungal dissemination from lungs to other target organ (i.e. spleen). Early and robust Th1 and Th17 cellular immunity in the lungs is critical for host to control pulmonary coccidioidal infection. We found that GCP-rCPA1 vaccinated mice had higher IFN-γ (Th1) and IL-17 (Th17) producing CD4+ cells in the lungs 7 days post *C. posadasii* and *C. immitis* challenge (FIG. 11).

Collectively, these data demonstrate that rCPA1 vaccination induces Th1/Th17 protective immunity and provides cross protection against both *C. posadasii* and *C. immitis*.

B. Materials and Methods
Vaccine preparations. Yeast cell-well particles derived from *Rhodotorula mucilaginosa* (GCPs) were prepared as previously reported (Young et al., 2007. *J Toxicol Environ Health A* 70:1116-24). Each dose of vaccine contained 10 μg rCpa1, 200 μg yeast tRNA and 25 μg mouse serum albumin (MSA) as a trapping matrix loaded into 400 μg of GCPs.

Vaccination protocol, animal challenge, and evaluation of protection. C57BL/6 mice were subcutaneously immunized twice in the abdominal region at a 2-week interval. Mice were challenged intranasally with a suspension of 80-100 viable spores of *C. posadasii* (C735, Silveria, 3844) or *C. immitis* (2394) in 35 μl of PBS 4 weeks after completion of the immunization protocol as previously reported (Hurtgen et al. 2012. *Infect Immun* 80:3960-74). Mice received GCPs containing 200 μg yeast tRNA and 25 μg MSA were used as non-vaccination controls. Mice were sacrificed at 14 days postchallenge for determination of the fungal burden in their lungs and spleen as previously described (Hurtgen et al. 2012. *Infect Immun* 80:3960-74; Xue et al., 2009. *Infect Immun* 77:3196-208; Hurtgen et al., 2016. *Vaccine* 34:5336-5343).

FACS analysis. Total pulmonary leukocytes were isolated from vaccinated and control mice at 7 days postchallenge (3 mice per group) as previously reported (Hung et al., 2011. *Infect Immun* 79:4511-22). A standard flow cytometry methodology was employed for direct monoclonal antibody (mAb) labeling and enumeration of selected pulmonary immune T cell phenotypes using a FACSCalibur cytometer as previously described (Hung et al., 2011. *Infect Immun* 79:4511-22). Permeabilized leukocytes were stained with a cocktail of fluorochrome-conjugated antibodies for IFN-γ, IL-17A, CD4 and CD8 molecules. Data was analyzed using FlowJo software version 10.

Statistical analyses. Student t-test was used to analyze results between two treatment groups for calculations of cell numbers of lung-infiltrated immune cells (Hung et al., 2014. *Infect Immun* 82:2106-14). The differences in fungal burdens (CFUs) between two groups were analyzed by the Mann-Whitney U ranking test (Hung et al., 2011. *Infect Immun* 79:4511-22). A p value of equal or less than 0.05 was considered statistically significant.

TABLE 1

Total of seven amino acid substitutions in the 6 vaccine antigens among isolates of Cp and Ci.
Amino Acid Substitutions*

| Antigens | Cp† | Ci† |
|---|---|---|
| Ag2/Pra | $D_{117}$ | $E_{117}$ |
| Cs—Ag | $A_{164}:P_{178}$ | $T_{164}:A_{178}$ |
| Pmp1 | $M_{424}:Q_{430}:I_{451}$ | $I_{424}:K_{430}:F_{481}$ |
| Amn1 | None | None |
| Pep | None | None |
| Plb | $W_{576}$ | $F_{576}$ |

*One letter amino acid abbreviation with a subscript number indicating position in rCpa1.
†Deduced amino acid sequences of each antigens for Cp and Ci were aligned using Multiple Sequence Alignment (ClustalW) tool.

SEQUENCE TABLE 2

```
>Results of amino acid sequence analysis (rCpa1_sequ) aligned with the
                       translated rCpa1 (rCpa1x0)

10         20         30         40         50         60
                          |          |          |          |          |          |
           rCpa1x0    MGSSHHHHHHSSGLVPRGSHMGPGPGMQFSHALIALVAAGLASAQLPDIPPCALNCFVEA
           rCpa1_sequ ------------------------------------------------------------
           Prim.cons. MGSSHHHHHHSSGLVPRGSHMGPGPGMQFSHALIALVAAGLASAQLPDIPPCALNCFVEA
```

SEQUENCE TABLE 2-continued

>Results of amino acid sequence analysis (rCpa1_sequ) aligned with the
translated rCpa1 (rCpa1x0)

```
                    70         80         90        100        110        120
                     |          |          |          |          |          |
rCpa1x0     LGNDGCTRLTDFKCHCSKPELPGQITPCVEEACPLDARISVSNIVVDQCSKAGVPIDIPP
rCpa1_sequ  ----------------------------------------ISVSNIVVDQCS----------
                                                    ************
Prim.cons.  LGNDGCTRLTDFKCHCSKPELPGQITPCVEEACPLDARISVSNIVVDQCSKAGVPIDIPP 130        140        150        160        170        180
                     |          |          |          |          |          |
rCpa1x0     VDTTAAPEPSETGPGPGMKFSLLSAIAAAVFVPFTSATPLASTADLSYDTHYDDPSLPLS
rCpa1_sequ  ------------------------------------------------------------
Prim.cons.  VDTTAAPEPSETGPGPGMKFSLLSAIAAAVFVPFTSATPLASTADLSYDTHYDDPSLPLS 190        200        210        220        230        240
                     |          |          |          |          |          |
rCpa1x0     GVTCSDGDNGMITKGYNTAGEIPNYPHVGGAFTVETWNSPNCGKCYKVTYNAKTIFLTAI
rCpa1_sequ  ------------------------------------------------------------
Prim.cons.  GVTCSDGDNGMITKGYNTAGEIPNYPHVGGAFTVETWNSPNCGKCYKVTYNAKTIFLTAI 250        260        270        280        290        300
                     |          |          |          |          |          |
rCpa1x0     DHSNSGFNIAKKSMDVLTNGRAEELGRIKVTYEEVASSLCGLKGPGPGMASLKAGDSFPS
rCpa1_sequ  -----------KSMDVLTNGR---------------------------------------
                       **********
Prim.cons.  DHSNSGFNIAKKSMDVLTNGRAEELGRIKVTYEEVASSLCGLKGPGPGMASLKAGDSFPS 310        320        330        340        350        360
                     |          |          |          |          |          |
rCpa1x0     DVVFSYIPWTPDNKDIKACGMPQNYEASKLWADKKVVLFSLPGAFTPTCSASHLPGYIQK
rCpa1_sequ  ------------------------------------------------------------
Prim.cons.  DVVFSYIPWTPDNKDIKACGMPQNYEASKLWADKKVVLFSLPGAFTPTCSASHLPGYIQK 370        380        390        400        410        420
                     |          |          |          |          |          |
rCpa1x0     LPQLKEKGVDVVAVLAFNDAWVMSAWGKANGVTGDDILFLSDPEAKFSKSIGWNAGERTG
rCpa1_sequ  ----------------------------ANGVTGDDILFLSDPEAK--------------
                                        ******************
Prim.cons.  LPQLKEKGVDVVAVLAFNDAWVMSAWGKANGVTGDDILFLSDPEAKFSKSIGWNAGERTG 430        440        450        460        470        480
                     |          |          |          |          |          |
rCpa1x0     RYAMIIDHGQVTYAEIEPGREVTVSGADAVISKLGPGPGMRNSILLAATVLLGCTSAKVH
rCpa1_sequ  -YAMIIDHGQVTYAEIEPGREVTVSGADAVIS----------------------------
             ********************************
Prim.cons.  RYAMIIDHGQVTYAEIEPGREVTVSGADAVISKLGPGPGMRNSILLAATVLLGCTSAKVH 490        500        510        520        530        540
                     |          |          |          |          |          |
rCpa1x0     GPGPGHVRALGQKYFGSLPSSQQQTVGPGPGPAKVDVLLAQSLKLADVLKFGPGPGNGLA
rCpa1_sequ  ------------KYFGSLPSSQQQTVGPGPGPAKVDVLLAQSLK----------------
                        ****************************
Prim.cons.  GPGPGHVRALGQKYFGSLPSSQQQTVGPGPGPAKVDVLLAQSLKLADVLKFGPGPGNGLA 550        560        570        580
                     |          |          |          |
rCpa1x0     TTGTLVLEWTRLSDITGPGPGTPLVVYIPNYPYTTWSNISTGPGPG
rCpa1_sequ  ----------------------------------------------
Prim.cons.  TTGTLVLEWTRLSDITGPGPGTPLVVYIPNYPYTTWSNISTGPGPG
```

REFERENCES

The following references, to the extent that they provide exemplary procedural or other details supplementary to those set forth herein, are specifically incorporated herein by reference.

MMWR C. 2013. Increase in reported coccidioidomycosis-United States, 1998-2011. MMWR Morb Mortal Wkly Rep 62:217-21.

Galgiani J N, Ampel N M, Blair J E, Catanzaro A, Geertsma F, Hoover S E, Johnson R H, Kusne S, Lisse J, MacDonald J D, Meyerson S L, Raksin P B, Siever J, Stevens D A, Sunenshine R, Theodore N. 2016. 2016 Infectious Diseases Society of America (IDSA) clinical practice guideline for the treatment of coccidioidomycosis. Clin Infect Dis 63:e112-46.

Thompson G R, 3rd. 2011. Pulmonary coccidioidomycosis. Semin Respir Crit Care Med 32:754-63.

Litvintseva A P, Marsden-Haug N, Hurst S, Hill H, Gade L, Driebe E M, Ralston C, Roe C, Barker B M, Goldoft M, Keim P, Wohrle R, Thompson G R, 3rd, Engelthaler D M, Brandt M E, Chiller T. 2015. Valley fever: finding new places for an old disease: *Coccidioides immitis* found in Washington state soil associated with recent human infection. Clin Infect Dis 60:e1-3.

Narra H P, Shubitz L F, Mandel M A, Trinh H T, Griffin K, Buntzman A S, Frelinger J A, Galgiani J N, Orbach M J. 2016. A *Coccidioides posadasii* CPS1 deletion mutant is avirulent and protects mice from lethal infection. Infect Immun 84:3007-16.

Hurtgen B J, Hung C Y, Ostroff G R, Levitz S M, Cole G T. 2012. Construction and evaluation of a novel recombinant T cell epitope-based vaccine against coccidioidomycosis. Infect Immun 80:3960-74.

Cole G T, Hurtgen B J, Hung C Y. 2012. Progress toward a human vaccine against coccidioidomycosis. Curr Fungal Infect Rep 6:235-244.

Cole G T, Xue J M, Okeke C N, Tarcha E J, Basrur V, Schaller R A, Herr R A, Yu J J, Hung C Y. 2004. A vaccine against coccidioidomycosis is justified and attainable. Med Mycol 42:189-216.

Orsbom K I, Shubitz L F, Peng T, Kellner E M, Orbach M J, Haynes P A, Galgiani J N. 2006. Protein expression profiling of *Coccidioides posadasii* by two-dimensional differential in-gel electrophoresis and evaluation of a newly recognized peroxisomal matrix protein as a recombinant vaccine candidate. Infect Immun 74:1865-72.

Tarcha E J, Basrur V, Hung C Y, Gardner M J, Cole G T. 2006. Multivalent recombinant protein vaccine against coccidioidomycosis. Infect Immun 74:5802-13.

Shubitz L F, Yu J J, Hung C Y, Kirkland T N, Peng T, Perrill R, Simons J, Xue J, Herr R A, Cole G T, Galgiani J N. 2006. Improved protection of mice against lethal respiratory infection with *Coccidioides posadasii* using two recombinant antigens expressed as a single protein. Vaccine 24:5904-11.

Azmi F, Ahmad Fuaad A A, Skwarczynski M, Toth I. 2014. Recent progress in adjuvant discovery for peptide-based subunit vaccines. Hum Vaccin Immunother 10:778-96.

Levitz S M, Golenbock D T. 2012. Beyond empiricism: informing vaccine development through innate immunity research. Cell 148:1284-92.

Xue J, Chen X, Selby D, Hung C Y, Yu J J, Cole G T. 2009. A genetically engineered live attenuated vaccine of *Coccidioides posadasii* protects BALB/c mice against coccidioidomycosis. Infect Immun 77:3196-208.

Wuthrich M, Hung C Y, Gem B H, Pick-Jacobs J C, Galles K J, Filutowicz H I, Cole G T, Klein B S. 2011. A TCR transgenic mouse reactive with multiple systemic dimorphic fungi. J Immunol 187:1421-31.

Hung C Y, Gonzalez A, Wuthrich M, Klein B S, Cole G T. 2011. Vaccine immunity to coccidioidomycosis occurs by early activation of three signal pathways of T helper cell response (Th1, Th2, and Th17). Infect Immun 79:4511-22.

Hung C Y, Hurtgen B J, Bellecourt M, Sanderson S D, Morgan E L, Cole G T. 2012. An agonist of human complement fragment C5a enhances vaccine immunity against *Coccidioides* infection. Vaccine 30:4681-90.

Young S H, Ostroff G R, Zeidler-Erdely P C, Roberts J R, Antonini J M, Castranova V. 2007. A comparison of the pulmonary inflammatory potential of different components of yeast cell wall. J Toxicol Environ Health A 70:1116-24.

Weitberg A B. 2008. A phase I/II trial of β-(1,3)/(1,6) D-glucan in the treatment of patients with advanced malignancies receiving chemotherapy. J Exp Clin Cancer Res 27:40.

Huang H, Ostroff G R, Lee C K, Agarwal S, Ram S, Rice P A, Specht C A, Levitz S M. 2012. Relative contributions of dectin-1 and complement to immune responses to particulate β-glucans. J Immunol 189:312-7.

Herr R A, Hung C Y, Cole G T. 2007. Evaluation of two homologous proline-rich proteins of *Coccidioides posadasii* as candidate vaccines against coccidioidomycosis. Infect Immun 75:5777-87.

Li K, Yu J J, Hung C Y, Lehmann P F, Cole G T. 2001. Recombinant urease and urease DNA of *Coccidioides immitis* elicit an immunoprotective response against coccidioidomycosis in mice. Infect Immun 69:2878-87.

Hurtgen B J, Hung C Y. 2017. Rational design of T lymphocyte epitope-based vaccines against *Coccidioides* infection. Methods Mol Biol 1625:45-64.

Hurtgen B J, Castro-Lopez N, Jimenez-Alzate M D P, Cole G T, Hung C Y. 2016. Preclinical identification of vaccine induced protective correlates in human leukocyte antigen expressing transgenic mice infected with *Coccidioides posadasii*. Vaccine 34:5336-5343.

Ji N, Kovalovsky A, Fingerle-Rowson G, Guentzel M N, Forsthuber T G. 2015. Macrophage migration inhibitory factor promotes resistance to glucocorticoid treatment in EAE. Neurol Neuroimmunol Neuroinflamm 2:e139.

Pan S, Cole G T. 1995. Molecular and biochemical characterization of a *Coccidioides immitis*-specific antigen. Infect Immun 63:3994-4002.

Pappagianis D. 1967. Histopathologic response of mice to killed vaccines of *Coccidioides immitis*. J Invest Dermatol 49:71-7.

Kirkland T. 2016. The quest for a vaccine against coccidioidomycosis: a neglected disease of the Americas. Journal of Fungi 2:34.

Levine H B, Pappagianis D, Cobb J M. 1970. Development of vaccines for coccidioidomycosis. Mycopathol Mycol Appl 41:177-85.

Pappagianis D. 1993. Evaluation of the protective efficacy of the killed *Coccidioides immitis* spherule vaccine in humans. Am Rev Respir Dis 148:656-60.

Kirkland T N, Fierer J. 1983. Inbred mouse strains differ in resistance to lethal *Coccidioides immitis* infection. Infect Immun 40:912-6.

Abuodeh R O, Shubitz L F, Siegel E, Snyder S, Peng T, Orsborn K I, Brummer E, Stevens D A, Galgiani J N. 1999. Resistance to *Coccidioides immitis* in mice after immunization with recombinant protein or a DNA vaccine of a proline-rich antigen. Infect Immun 67:2935-40.

Neafsey D E, Barker B M, Sharpton T J, Stajich J E, Park D J, Whiston E, Hung C Y, McMahan C, White J, Sykes S, Heiman D, Young S, Zeng Q, Abouelleil A, Aftuck L, Bessette D, Brown A, FitzGerald M, Lui A, Macdonald J P, Priest M, Orbach M J, Galgiani J N, Kirkland T N, Cole G T, Birren B W, Henn M R, Taylor J W, Rounsley S D. 2010. Population genomic sequencing of *Coccidioides* fungi reveals recent hybridization and transposon control. Genome Res 20:938-46.

Galgiani J N, Sun S H, Dugger K O, Ampel N M, Grace G G, Harrison J, Wieden M A. 1992. An arthroconidial-spherule antigen of *Coccidioides immitis*: differential expression during in vitro fungal development and evidence for humoral response in humans after infection or vaccination. Infect Immun 60:2627-35.

Gow N A R, Latge J P, Munro C A. 2017. The fungal cell wall: structure, biosynthesis, and function. Microbiol Spectr 5.

Taylor P R, Tsoni S V, Willment J A, Dennehy K M, Rosas M, Findon H, Haynes K, Steele C, Botto M, Gordon S, Brown G D. 2007. Dectin-1 is required for β-glucan recognition and control of fungal infection. Nat Immunol 8:31-8.

Da Silva C A, Hard D, Liu W, Lee C G, Elias J A. 2008. TLR-2 and IL-17A in chitin-induced macrophage activation and acute inflammation. J Immunol 181:4279-4286.

Schlosser A, Thomsen T, Moeller J B, Nielsen O, Tornoe I, Mollenhauer J, Moestrup S K, Holmskov U. 2009. Characterization of FIBCD1 as an acetyl group-binding receptor that binds chitin. J Immunol 183:3800-3809.

Wagener J, Malireddi R K, Lenardon M D, Koberle M, Vautier S, MacCallum D M, Biedermann T, Schaller M, Netea M G, Kanneganti T D, Brown G D, Brown A J, Gow N A. 2014. Fungal chitin dampens inflammation through IL-10 induction mediated by NOD2 and TLR9 activation. PLoS Pathog 10:e1004050.

Ito K, Bian H J, Molina M, Han J, Magram J, Saar E, Belunis C, Bolin D R, Arceo R, Campbell R, Falcioni F, Vidovic D, Hammer J, Nagy Z A. 1996. HLA-DR4-IE chimeric class II transgenic, murine class II-deficient mice are susceptible to experimental allergic encephalomyelitis. J Exp Med 183:2635-44.

Xue J, Hung C Y, Yu J J, Cole G T. 2005. Immune response of vaccinated and non-vaccinated mice to *Coccidioides posadasii* infection. Vaccine 23:3535-44.

Hung C Y, Castro-Lopez N, Cole G T. 2016. Card9- and MyD88-mediated gamma-Interferon and nitric oxide production is essential for resistance to subcutaneous *Coccidioides posadasii* infection. Infect Immun 84:1166-75.

Hung C Y, Jimenez-Alzate Mdel P, Gonzalez A, Wuthrich M, Klein B S, Cole G T. 2014. Interleukin-1 receptor but not Toll-like receptor 2 is essential for MyD88-dependent Th17 immunity to *Coccidioides* infection. Infect Immun 82:2106-14. Hurtgen, B. J. et al, (2012). "Construction and evaluation of a novel recombinant T cell epitope-based vaccine against Coccidioidomycosis." *Infect Immun* 80(11): 3960-3974.

Hurtgen, B. J. and C. Y. Hung (2017). "Rational Design of T Lymphocyte Epitope-Based Vaccines Against *Coccidioides* Infection." *Methods Mol Biol* 1625: 45-64.

Orsborn, K. I. et al, (2006). "Protein expression profiling of *Coccidioides posadasii* by two-dimensional differential in-gel electrophoresis and evaluation of a newly recognized peroxisomal matrix protein as a recombinant vaccine candidate." *Infect Immun* 74(3): 1865-1872.

Shubitz, L. F. et al, (2006). "Improved protection of mice against lethal respiratory infection with *Coccidioides posadasii* using two recombinant antigens expressed as a single protein." *Vaccine* 24(31-32): 5904-5911.

Rational design of antigens and adjuvants for enhancement of vaccine potency. Invited speaker, Biology Department, UTSA. San Antonio, Tex. 78249. Dec. 8, 2016.

Determinants of a vaccine for coccidioidomycosis. Invited speaker. 7$^{th}$ International coccidioidomycosis symposium. Stanford, Calif. Aug. 10-13, 2017.

Kohler and Milstein, Nature 256:495-497, 1975.

Harlow and Lane, *Antibodies: A Laboratory Manual*, Cold Spring Harbor Laboratory, Cold Spring Harbor, N.Y., Chapter 8, 1988.

Vaughan, et al., Nat. Biotech. 16; 535-539, 1998.

Remington's Pharmaceutical Sciences, 18th Ed. Mack Printing Company, 1289-1329, 1990.

Mosmann and Coffman, Ann. Rev. Immunol., 7:145-173, 1989.

Thomson et al., J. Immunol., 157(2):822-826, 1996.

An, J. Virol., 71(3):2292-302, 1997.

Tigges et al., J. Immunol., 156(10):3901-3910, 1996.

Burke et al., J. Inf. Dis., 170:1110-1119, 1994.

Pelletier and Sonenberg, Nature, 334(6180):320-325, 1988.

Macejak and Sarnow, Nature, 353:90-94, 1991.

Devereux et al., Nucl. Acid Res., 12:387-395, 1984.

Pearson and Lipman, Proc. Natl. Acad. Sci. USA, 85:2444, 1988.

Needleman and Wunsch, J. Mol. Biol., 48:443, 1970.

Smith and Waterman, Adv. Appl. Math., 2:482, 1981.

U.S. Pat. No. 7,332,324 B2: Attenuated vaccine useful for immunizations against *Coccidioides* spp. Infections

---

SEQUENCE LISTING

```
<160> NUMBER OF SEQ ID NOS: 8

<210> SEQ ID NO 1
<211> LENGTH: 1758
<212> TYPE: DNA
<213> ORGANISM: Coccidioides immitis
<220> FEATURE:
<221> NAME/KEY: CDS
<222> LOCATION: (1)..(1758)

<400> SEQUENCE: 1 atg ggc agc agc cat cat cat cat cat cac agc agc ggc ctg gtg ccg      48
Met Gly Ser Ser His His His His His His Ser Ser Gly Leu Val Pro
1               5                   10                  15 cgc ggc agc cat atg ggc ccg ggt ccg ggt atg cag ttc agc cac gcg      96
Arg Gly Ser His Met Gly Pro Gly Pro Gly Met Gln Phe Ser His Ala
            20                  25                  30 ctg atc gcg ctg gtt gca gcg ggt ctg gct tcc gca cag ctg ccg gac     144
Leu Ile Ala Leu Val Ala Ala Gly Leu Ala Ser Ala Gln Leu Pro Asp
        35                  40                  45 atc ccg ccg tgc gct ctg aac tgt ttc gtg gag gcg ctg ggc aac gat     192
Ile Pro Pro Cys Ala Leu Asn Cys Phe Val Glu Ala Leu Gly Asn Asp
    50                  55                  60 ggt tgt act cgt ctg acc gac ttt aaa tgt cac tgc tcc aaa ccg gag     240
Gly Cys Thr Arg Leu Thr Asp Phe Lys Cys His Cys Ser Lys Pro Glu
65                  70                  75                  80
```

| | | |
|---|---|---|
| ctg ccg ggt cag att act ccg tgc gtt gaa gaa gcg tgc ccg ctg gac<br>Leu Pro Gly Gln Ile Thr Pro Cys Val Glu Glu Ala Cys Pro Leu Asp<br>85　　　　　　　　90　　　　　　　　95 | | 288 |
| gcg cgc atc tct gtt tct aac att gtt gtt gac cag tgt tct aaa gcg<br>Ala Arg Ile Ser Val Ser Asn Ile Val Val Asp Gln Cys Ser Lys Ala<br>100　　　　　　　　105　　　　　　　　110 | | 336 |
| ggt gtt ccg att gac att ccg ccg gtt gat acc act gct gcg ccg gaa<br>Gly Val Pro Ile Asp Ile Pro Pro Val Asp Thr Thr Ala Ala Pro Glu<br>115　　　　　　　　120　　　　　　　　125 | | 384 |
| ccg tcc gaa acc ggc ccg ggt ccg ggc atg aaa ttt agc ctg ctg tcc<br>Pro Ser Glu Thr Gly Pro Gly Pro Gly Met Lys Phe Ser Leu Leu Ser<br>130　　　　　　　　135　　　　　　　　140 | | 432 |
| gct atc gca gcg gcg gtt ttc gtt ccg ttt act agc gcg acc ccg ctg<br>Ala Ile Ala Ala Ala Val Phe Val Pro Phe Thr Ser Ala Thr Pro Leu<br>145　　　　　　　　150　　　　　　　　155　　　　　　　　160 | | 480 |
| gca tct acc gcg gac ctg tct tac gac acc cac tac gac gat ccg tct<br>Ala Ser Thr Ala Asp Leu Ser Tyr Asp Thr His Tyr Asp Asp Pro Ser<br>165　　　　　　　　170　　　　　　　　175 | | 528 |
| ctg ccg ctg tct ggc gtt act tgc tct gat ggt gac aac ggt atg atc<br>Leu Pro Leu Ser Gly Val Thr Cys Ser Asp Gly Asp Asn Gly Met Ile<br>180　　　　　　　　185　　　　　　　　190 | | 576 |
| acc aaa ggt tac aac acc gcg ggt gag att ccg aac tac ccg cac gtt<br>Thr Lys Gly Tyr Asn Thr Ala Gly Glu Ile Pro Asn Tyr Pro His Val<br>195　　　　　　　　200　　　　　　　　205 | | 624 |
| ggt ggt gca ttc acc gtg gaa acc tgg aac tct ccg aac tgc ggt aaa<br>Gly Gly Ala Phe Thr Val Glu Thr Trp Asn Ser Pro Asn Cys Gly Lys<br>210　　　　　　　　215　　　　　　　　220 | | 672 |
| tgc tat aaa gtg act tac aac gct aag acc atc ttc ctg act gcg atc<br>Cys Tyr Lys Val Thr Tyr Asn Ala Lys Thr Ile Phe Leu Thr Ala Ile<br>225　　　　　　　　230　　　　　　　　235　　　　　　　　240 | | 720 |
| gac cac tct aac tct ggt ttc aac atc gcg aaa aaa tct atg gac gtt<br>Asp His Ser Asn Ser Gly Phe Asn Ile Ala Lys Lys Ser Met Asp Val<br>245　　　　　　　　250　　　　　　　　255 | | 768 |
| ctg act aac ggt cgt gca gaa gaa ctg ggc cgt atc aaa gtt acc tac<br>Leu Thr Asn Gly Arg Ala Glu Glu Leu Gly Arg Ile Lys Val Thr Tyr<br>260　　　　　　　　265　　　　　　　　270 | | 816 |
| gag gaa gtt gca tcc tcc ctg tgt ggt ctg aaa ggc ccg ggt ccg ggc<br>Glu Glu Val Ala Ser Ser Leu Cys Gly Leu Lys Gly Pro Gly Pro Gly<br>275　　　　　　　　280　　　　　　　　285 | | 864 |
| atg gca tcc ctg aag gca ggc gat tct ttc ccg tct gat gtt gtt ttt<br>Met Ala Ser Leu Lys Ala Gly Asp Ser Phe Pro Ser Asp Val Val Phe<br>290　　　　　　　　295　　　　　　　　300 | | 912 |
| tct tat att ccg tgg acc ccg gac aac aaa gac atc aaa gcg tgt ggt<br>Ser Tyr Ile Pro Trp Thr Pro Asp Asn Lys Asp Ile Lys Ala Cys Gly<br>305　　　　　　　　310　　　　　　　　315　　　　　　　　320 | | 960 |
| atg ccg cag aac tac gaa gcg tct aaa ctg tgg gcg gac aaa aaa gtt<br>Met Pro Gln Asn Tyr Glu Ala Ser Lys Leu Trp Ala Asp Lys Lys Val<br>325　　　　　　　　330　　　　　　　　335 | | 1008 |
| gtg ctg ttt tcc ctg ccg ggt gcg ttt acc ccg acc tgc tct gcg tct<br>Val Leu Phe Ser Leu Pro Gly Ala Phe Thr Pro Thr Cys Ser Ala Ser<br>340　　　　　　　　345　　　　　　　　350 | | 1056 |
| cat ctg ccg ggt tac att cag aaa ctg ccg cag ctg aag gaa aaa ggt<br>His Leu Pro Gly Tyr Ile Gln Lys Leu Pro Gln Leu Lys Glu Lys Gly<br>355　　　　　　　　360　　　　　　　　365 | | 1104 |
| gtt gac gtt gtt gcg gtt ctg gca ttc aac gac gcg tgg gtt atg tct<br>Val Asp Val Val Ala Val Leu Ala Phe Asn Asp Ala Trp Val Met Ser<br>370　　　　　　　　375　　　　　　　　380 | | 1152 |
| gcg tgg ggt aag gcg aac ggt gtt act ggt gac gac atc ctg ttc ctg<br>Ala Trp Gly Lys Ala Asn Gly Val Thr Gly Asp Asp Ile Leu Phe Leu | | 1200 |

```
                385                 390                 395                 400
tcc gat ccg gaa gcg aaa ttc tct aaa tcc att ggt tgg aac gca ggt       1248
Ser Asp Pro Glu Ala Lys Phe Ser Lys Ser Ile Gly Trp Asn Ala Gly
                405                 410                 415 gaa cgt acc ggt cgt tat gcg atg att att gat cat ggt cag gtg acc       1296
Glu Arg Thr Gly Arg Tyr Ala Met Ile Ile Asp His Gly Gln Val Thr
            420                 425                 430 tac gcg gaa atc gaa ccg ggt cgt gaa gtg acc gtg tcc ggt gct gat       1344
Tyr Ala Glu Ile Glu Pro Gly Arg Glu Val Thr Val Ser Gly Ala Asp
                435                 440                 445 gct gtg att tct aag ctg ggc ccg ggt ccg ggc atg cgc aac tct atc       1392
Ala Val Ile Ser Lys Leu Gly Pro Gly Pro Gly Met Arg Asn Ser Ile
        450                 455                 460 ctg ctg gca gct acc gtg ctg ctg ggt tgc act tct gcg aag gtt cat       1440
Leu Leu Ala Ala Thr Val Leu Leu Gly Cys Thr Ser Ala Lys Val His
465                 470                 475                 480 ggc ccg ggt ccg ggt cac gtt cgt gct ctg ggc cag aaa tac ttc ggc       1488
Gly Pro Gly Pro Gly His Val Arg Ala Leu Gly Gln Lys Tyr Phe Gly
                485                 490                 495 agc ctg ccg tcc tct cag cag cag acc gtt ggc ccg ggt ccg ggc ccg       1536
Ser Leu Pro Ser Ser Gln Gln Gln Thr Val Gly Pro Gly Pro Gly Pro
                500                 505                 510 gca aaa gtg gat gtt ctg ctg gct cag tct ctg aag ctg gcg gac gtg       1584
Ala Lys Val Asp Val Leu Leu Ala Gln Ser Leu Lys Leu Ala Asp Val
            515                 520                 525 ctg aag ttt ggc ccg ggt ccg ggt aac ggc ctg gcg acc acc ggc acc       1632
Leu Lys Phe Gly Pro Gly Pro Gly Asn Gly Leu Ala Thr Thr Gly Thr
        530                 535                 540 ctg gtg ctg gag tgg act cgc ctg tct gac atc acc ggc ccg ggt ccg       1680
Leu Val Leu Glu Trp Thr Arg Leu Ser Asp Ile Thr Gly Pro Gly Pro
545                 550                 555                 560 ggt act ccg ctg gtg gtt tat atc ccg aac tat ccg tac acc acc tgg       1728
Gly Thr Pro Leu Val Val Tyr Ile Pro Asn Tyr Pro Tyr Thr Thr Trp
                565                 570                 575 agc aac atc tct act ggc ccg ggt ccg ggt                               1758
Ser Asn Ile Ser Thr Gly Pro Gly Pro Gly
                580                 585

<210> SEQ ID NO 2
<211> LENGTH: 586
<212> TYPE: PRT
<213> ORGANISM: Coccidioides immitis

<400> SEQUENCE: 2

Met Gly Ser Ser His His His His Ser Ser Gly Leu Val Pro
1               5                   10                  15

Arg Gly Ser His Met Gly Pro Gly Pro Gly Met Gln Phe Ser His Ala
                20                  25                  30

Leu Ile Ala Leu Val Ala Ala Gly Leu Ala Ser Ala Gln Leu Pro Asp
            35                  40                  45

Ile Pro Pro Cys Ala Leu Asn Cys Phe Val Glu Ala Leu Gly Asn Asp
        50                  55                  60

Gly Cys Thr Arg Leu Thr Asp Phe Lys Cys His Cys Ser Lys Pro Glu
65                  70                  75                  80

Leu Pro Gly Gln Ile Thr Pro Cys Val Glu Glu Ala Cys Pro Leu Asp
                85                  90                  95

Ala Arg Ile Ser Val Ser Asn Ile Val Val Asp Gln Cys Ser Lys Ala
                100                 105                 110
```

```
Gly Val Pro Ile Asp Ile Pro Pro Val Asp Thr Thr Ala Pro Glu
            115                 120                 125
Pro Ser Glu Thr Gly Pro Gly Pro Gly Met Lys Phe Ser Leu Leu Ser
    130                 135                 140
Ala Ile Ala Ala Ala Val Phe Val Pro Phe Thr Ser Ala Thr Pro Leu
145                 150                 155                 160
Ala Ser Thr Ala Asp Leu Ser Tyr Asp Thr His Tyr Asp Asp Pro Ser
                165                 170                 175
Leu Pro Leu Ser Gly Val Thr Cys Ser Asp Gly Asp Asn Gly Met Ile
                180                 185                 190
Thr Lys Gly Tyr Asn Thr Ala Gly Glu Ile Pro Asn Tyr Pro His Val
                195                 200                 205
Gly Gly Ala Phe Thr Val Glu Thr Trp Asn Ser Pro Asn Cys Gly Lys
            210                 215                 220
Cys Tyr Lys Val Thr Tyr Asn Ala Lys Thr Ile Phe Leu Thr Ala Ile
225                 230                 235                 240
Asp His Ser Asn Ser Gly Phe Asn Ile Ala Lys Lys Ser Met Asp Val
                245                 250                 255
Leu Thr Asn Gly Arg Ala Glu Glu Leu Gly Arg Ile Lys Val Thr Tyr
                260                 265                 270
Glu Glu Val Ala Ser Ser Leu Cys Gly Leu Lys Gly Pro Gly Pro Gly
            275                 280                 285
Met Ala Ser Leu Lys Ala Gly Asp Ser Phe Pro Ser Asp Val Val Phe
            290                 295                 300
Ser Tyr Ile Pro Trp Thr Pro Asp Asn Lys Asp Ile Lys Ala Cys Gly
305                 310                 315                 320
Met Pro Gln Asn Tyr Glu Ala Ser Lys Leu Trp Ala Asp Lys Lys Val
                325                 330                 335
Val Leu Phe Ser Leu Pro Gly Ala Phe Thr Pro Thr Cys Ser Ala Ser
                340                 345                 350
His Leu Pro Gly Tyr Ile Gln Lys Leu Pro Gln Leu Lys Glu Lys Gly
            355                 360                 365
Val Asp Val Val Ala Val Leu Ala Phe Asn Asp Ala Trp Val Met Ser
            370                 375                 380
Ala Trp Gly Lys Ala Asn Gly Val Thr Gly Asp Asp Ile Leu Phe Leu
385                 390                 395                 400
Ser Asp Pro Glu Ala Lys Phe Ser Lys Ser Ile Gly Trp Asn Ala Gly
                405                 410                 415
Glu Arg Thr Gly Arg Tyr Ala Met Ile Ile Asp His Gly Gln Val Thr
                420                 425                 430
Tyr Ala Glu Ile Glu Pro Gly Arg Glu Val Thr Val Ser Gly Ala Asp
            435                 440                 445
Ala Val Ile Ser Lys Leu Gly Pro Gly Pro Gly Met Arg Asn Ser Ile
            450                 455                 460
Leu Leu Ala Ala Thr Val Leu Leu Gly Cys Thr Ser Ala Lys Val His
465                 470                 475                 480
Gly Pro Gly Pro Gly His Val Arg Ala Leu Gly Gln Lys Tyr Phe Gly
                485                 490                 495
Ser Leu Pro Ser Ser Gln Gln Thr Val Gly Pro Gly Pro Gly Pro
            500                 505                 510
Ala Lys Val Asp Val Leu Leu Ala Gln Ser Leu Lys Leu Ala Asp Val
            515                 520                 525
Leu Lys Phe Gly Pro Gly Pro Gly Asn Gly Leu Ala Thr Thr Gly Thr
```

```
                  530                 535                 540
Leu Val Leu Glu Trp Thr Arg Leu Ser Asp Ile Thr Gly Pro Gly Pro
545                 550                 555                 560

Gly Thr Pro Leu Val Val Tyr Ile Pro Asn Tyr Pro Tyr Thr Thr Trp
                565                 570                 575

Ser Asn Ile Ser Thr Gly Pro Gly Pro Gly
                580                 585
```

<210> SEQ ID NO 3
<211> LENGTH: 21
<212> TYPE: PRT
<213> ORGANISM: Artificial Sequence
<220> FEATURE:
<223> OTHER INFORMATION: Synthetic peptide

<400> SEQUENCE: 3

```
Met Arg Asn Ser Ile Leu Leu Ala Ala Thr Val Leu Leu Gly Cys Thr
1               5                   10                  15

Ser Ala Lys Val His
            20
```

<210> SEQ ID NO 4
<211> LENGTH: 21
<212> TYPE: PRT
<213> ORGANISM: Artificial Sequence
<220> FEATURE:
<223> OTHER INFORMATION: Synthetic peptide

<400> SEQUENCE: 4

```
His Val Arg Ala Leu Gly Gln Lys Tyr Phe Gly Ser Leu Pro Ser Ser
1               5                   10                  15

Gln Gln Gln Thr Val
            20
```

<210> SEQ ID NO 5
<211> LENGTH: 20
<212> TYPE: PRT
<213> ORGANISM: Artificial Sequence
<220> FEATURE:
<223> OTHER INFORMATION: Synthetic peptide

<400> SEQUENCE: 5

```
Pro Ala Lys Val Asp Val Leu Leu Ala Gln Ser Leu Lys Leu Ala Asp
1               5                   10                  15

Val Leu Lys Phe
            20
```

<210> SEQ ID NO 6
<211> LENGTH: 20
<212> TYPE: PRT
<213> ORGANISM: Artificial Sequence
<220> FEATURE:
<223> OTHER INFORMATION: Synthetic peptide

<400> SEQUENCE: 6

```
Asn Gly Leu Ala Thr Thr Gly Thr Leu Val Leu Glu Trp Thr Arg Leu
1               5                   10                  15

Ser Asp Ile Thr
            20
```

<210> SEQ ID NO 7
<211> LENGTH: 20
<212> TYPE: PRT

-continued

```
<213> ORGANISM: Artificial Sequence
<220> FEATURE:
<223> OTHER INFORMATION: synthetic peptide

<400> SEQUENCE: 7

Thr Pro Leu Val Val Tyr Ile Pro Asn Tyr Pro Tyr Thr Thr Trp Ser
1               5                   10                  15

Asn Ile Ser Thr
            20

<210> SEQ ID NO 8
<211> LENGTH: 5
<212> TYPE: PRT
<213> ORGANISM: Artificial Sequence
<220> FEATURE:
<223> OTHER INFORMATION: synthetic peptide

<400> SEQUENCE: 8

Gly Pro Gly Pro Gly
1               5
```

The invention claimed is:

1. An immunogenic composition comprising a recombinant *Coccidioides* polypeptide antigen (rCpa1) having an amino acid sequence at least 80% identical to SEQ ID NO:2.

2. The composition of claim 1, wherein the rCpa1 antigen has an amino acid sequence at least 80% identical to amino acids 11 to 586 SEQ ID NO:2.

3. The composition of claim 1, wherein the rCpa1 antigen is comprised in a yeast cell-wall particle.

4. The composition of claim 3, wherein the yeast cell-wall particle is a β-glucan particle (GP), glucan-mannan particle (GMC), glucan-chitin particle (GCP), and glucan-chitin-mannan particle (GCMP).

5. The composition of claim 1, wherein the composition further comprises a CpG oligonucleotide.

6. A method of treating a subject having or at risk of *Coccidioides* infection comprising administering an effective amount of a composition of claim 1.

7. The method of claim 6, further comprising administering a CpG oligonucleotide.

8. A polynucleotide encoding a recombinant *Coccidioides* polypeptide antigen (rCpa1) having an amino acid sequence at least 80% identical to SEQ ID NO:2.

9. The polynucleotide of claim 8, wherein the polynucleotide is an expression vector.

10. The composition of claim 1, wherein the rCpa1 antigen has an amino acid sequence of SEQ ID NO:2.

11. The composition of claim 1, wherein the rCpa1 antigen has an amino acid sequence of amino acids 11 to 586 SEQ ID NO:2.

* * * * *